US009708252B2

(12) United States Patent
Negishi et al.

(10) Patent No.: US 9,708,252 B2
(45) Date of Patent: Jul. 18, 2017

(54) FATTY ACID ALKYL ESTER SULFONATE METAL SALT POWDER MIXTURE AND METHOD FOR PRODUCING THE SAME

(75) Inventors: Daisuke Negishi, Tokyo (JP); Masahiko Matsubara, Tokyo (JP); Yuki Nishiyama, Tokyo (JP); Kensuke Itakura, Tokyo (JP); Kenji Morimura, Tokyo (JP)

(73) Assignee: LION CORPORATION, Tokyo (JP)

( * ) Notice: Subject to any disclaimer, the term of this patent is extended or adjusted under 35 U.S.C. 154(b) by 203 days.

(21) Appl. No.: 13/265,724

(22) PCT Filed: Apr. 22, 2010

(86) PCT No.: PCT/JP2010/057137
§ 371 (c)(1),
(2), (4) Date: Jan. 9, 2012

(87) PCT Pub. No.: WO2010/123060
PCT Pub. Date: Oct. 28, 2010

(65) Prior Publication Data
US 2012/0115770 A1 May 10, 2012

(30) Foreign Application Priority Data
Apr. 22, 2009 (JP) .................................. 2009-104010

(51) Int. Cl.
*C11D 1/12* (2006.01)
*C11D 17/06* (2006.01)
(Continued)

(52) U.S. Cl.
CPC .............. *C07C 309/17* (2013.01); *C11D 1/12* (2013.01); *C11D 1/28* (2013.01); *C11D 17/06* (2013.01)

(58) Field of Classification Search
CPC .................................. C11D 1/12; C11D 17/06
(Continued)

(56) References Cited

U.S. PATENT DOCUMENTS

| 7,592,302 | B2 * | 9/2009 | Itakura et al. ................. 510/446 |
| 8,501,972 | B2 * | 8/2013 | Abe et al. ......................... 554/97 |
| 2006/0160717 | A1 * | 7/2006 | Itakura et al. ................. 510/447 |

FOREIGN PATENT DOCUMENTS

| JP | 62-298570 A | 12/1987 |
| JP | 8-318149 A | 12/1996 |

(Continued)

OTHER PUBLICATIONS

Fujiwara, M., et al. "Phase Diagram of α-Sulfonated Palmitic Acid Methyl Ester Sodium Salt-Water System," Langmuir, 1997, pp. 3345-3348, vol. No. 13, American Chemical Society.

*Primary Examiner* — Gregory R Delcotto
(74) *Attorney, Agent, or Firm* — Nath, Goldberg & Meyer; Joshua B. Goldberg; Annie Kock

(57) ABSTRACT

The invention provides a fatty acid alkyl ester sulfonate metal salt mixture of (a) a fatty acid alkyl ester sulfonate metal salt having an endothermic peak area at 50 to 130° C. of less than 50% relative to the whole endothermic peak area at 0 to 130° C. as measured on a differential scanning calorimeter, and (b) a fatty acid alkyl ester sulfonate metal salt having an endothermic peak area at 50 to 130° C. of 50% or more relative to the whole endothermic peak area at 0 to 130° C. as measured on a differential scanning calorimeter, with a ratio of (a) to (b) by mass of 95/5 or less. The mixture of the invention is excellent in anti-caking properties.

6 Claims, 13 Drawing Sheets

(51) Int. Cl.
*C07C 309/17* (2006.01)
*C11D 1/28* (2006.01)

(58) Field of Classification Search
USPC ....... 510/156, 220, 351, 357, 428, 492, 445, 510/446; 554/97, 85, 88, 96
See application file for complete search history.

(56) References Cited

FOREIGN PATENT DOCUMENTS

| | | |
|---|---|---|
| JP | 10-298159 A | 11/1998 |
| WO | 2004/111166 A1 | 12/2004 |
| WO | 2008/078609 A1 | 7/2008 |
| WO | 2009/054406 A1 | 4/2009 |

\* cited by examiner

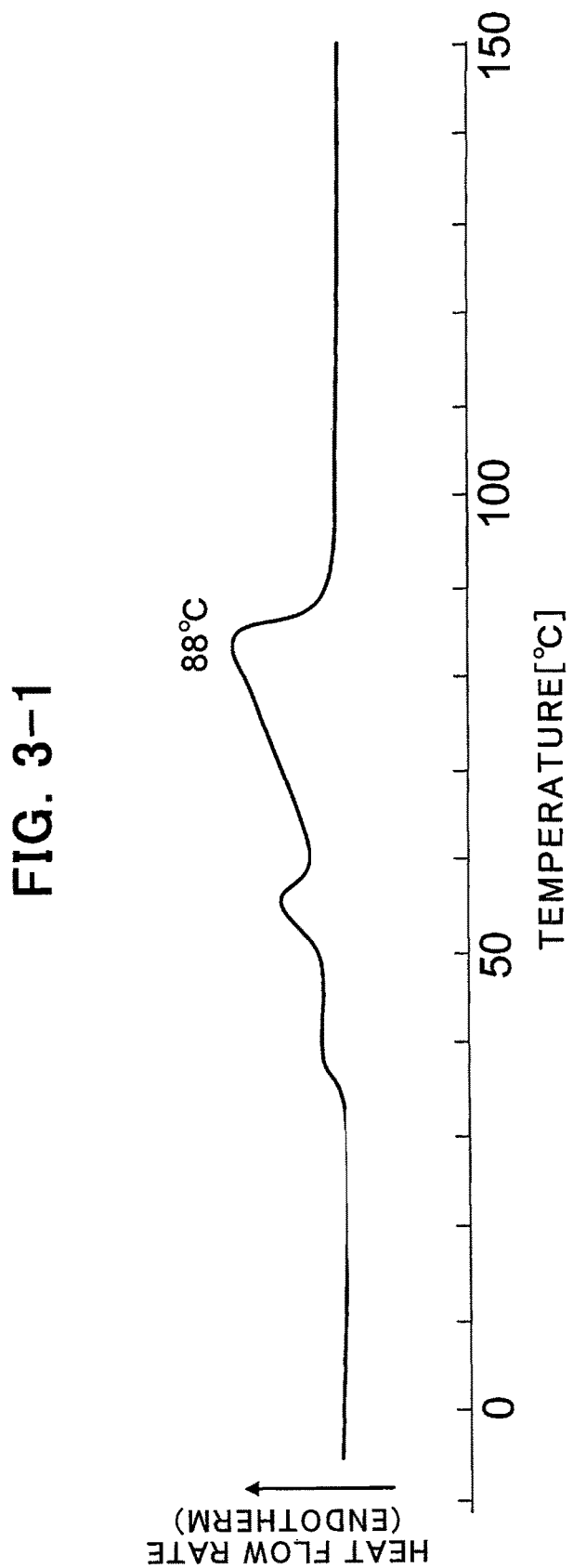

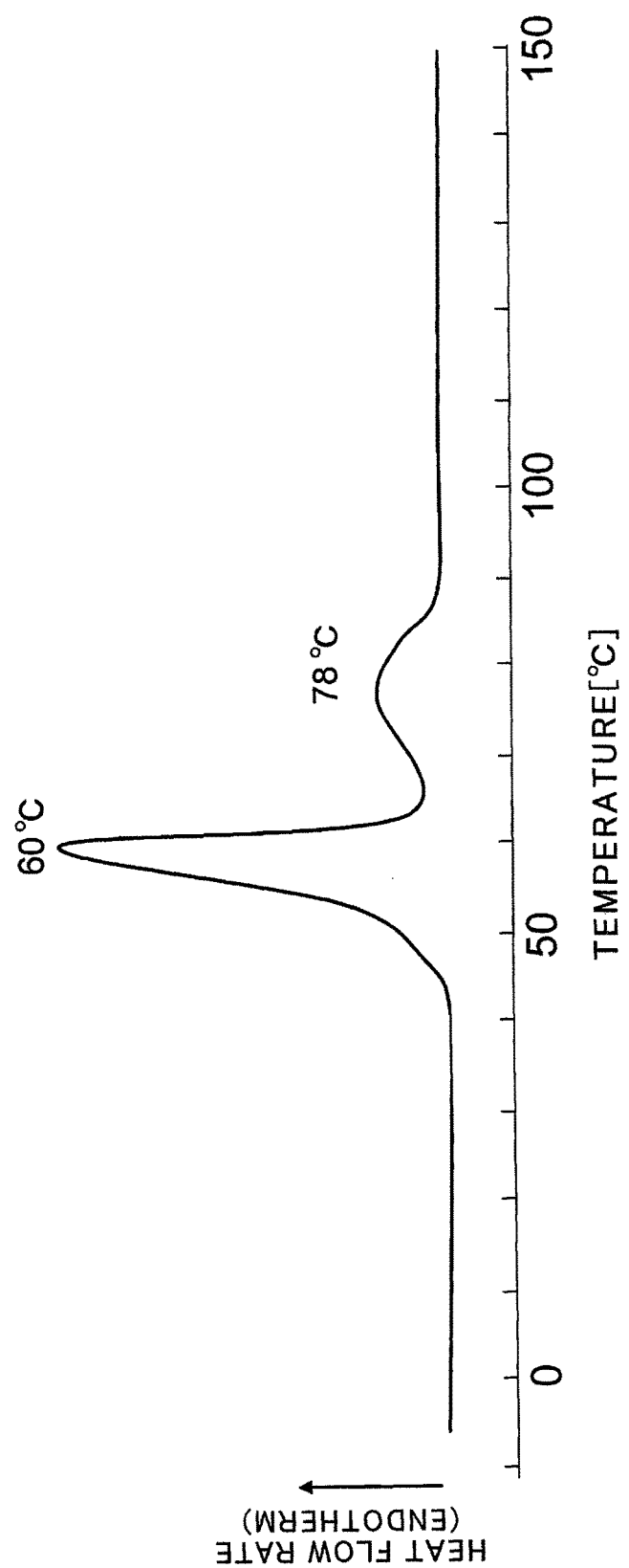

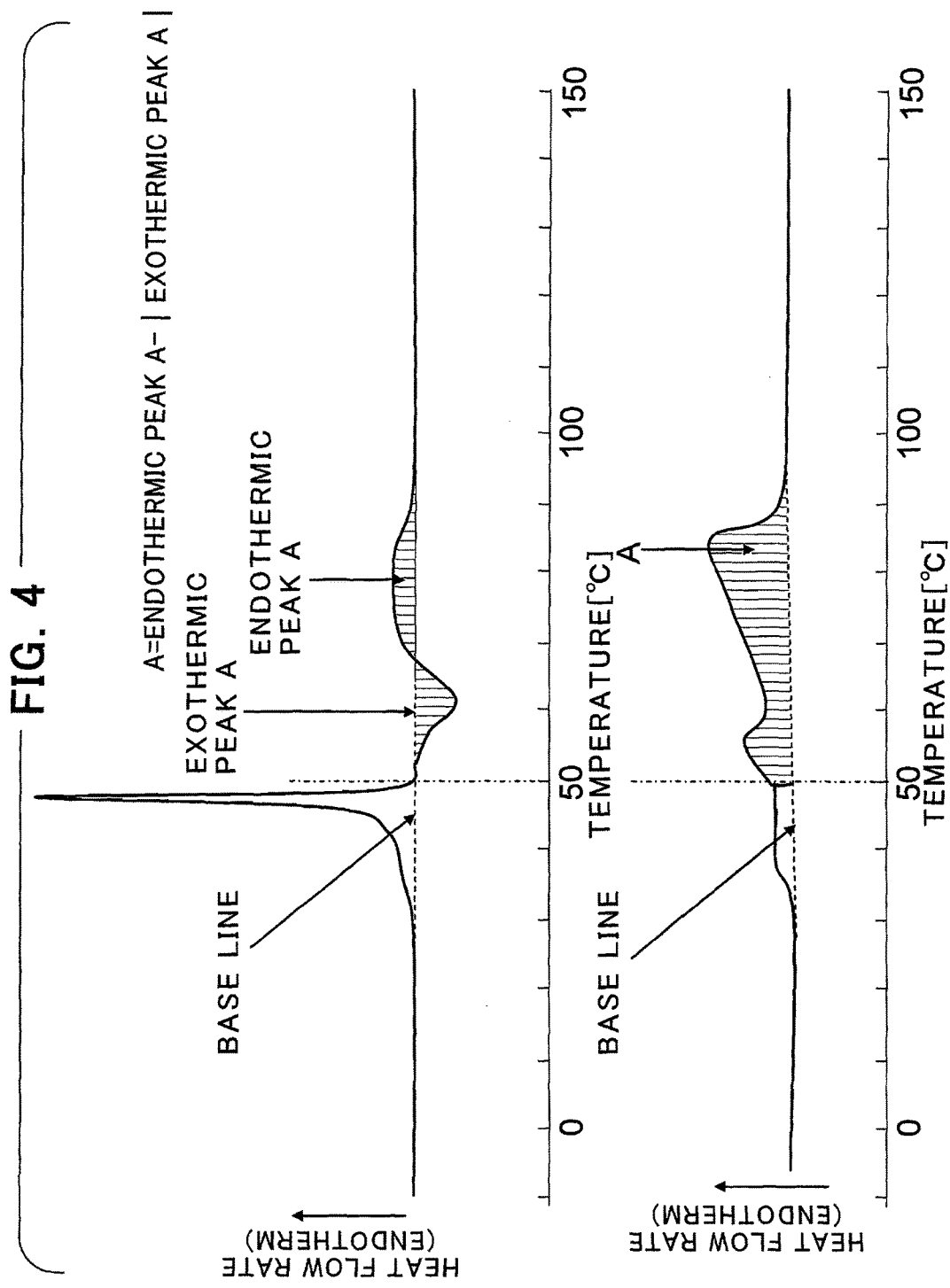

FATTY ACID ALKYL ESTER SULFONATE METAL SALT POWDER MIXTURE AND METHOD FOR PRODUCING THE SAME

This is a National Phase Application filed under 35 U.S.C. §371 as a national stage of International Application No. PCT/JP2010/057137, filed Apr. 22, 2010, claiming the benefit from Japanese Patent Application No. 2009-104010, filed Apr. 22, 2009, the entire content of each of which is hereby incorporated by reference in its entirety.

FIELD OF THE INVENTION

The present invention relates to a fatty acid alkyl ester sulfonate metal salt powder mixture and a method for producing the above-mentioned mixture.

BACKGROUND OF THE INVENTION

The fatty acid alkyl ester sulfonate metal salt is also referred to as α-sulfo fatty acid alkyl ester salt or α-SF salt, which is mainly used as the material for granular detergents for clothes (WO2004/111166). The methyl ester salt (MES) is most widely used as the material for granular detergents.

To produce the granular detergent, for example, the α-SF salt in a slurry form is concentrated to obtain a solid, and then the solid is ground into powders. Those powders are dry-blended with other surfactants, builders and the like, thereby producing the granular detergent. When the α-SF salt is transported to the place for dry-blending, the α-SF salt in a solid form such as flakes or pellets is more convenient than the salt in a liquid form such as a paste or concentrate.

However, the solid products may cause agglomeration to form cakes under the circumstances of heavy load or high temperatures during the transportation. This will hinder the process subsequent to the transportation and worsen the handling properties.

Accordingly, it is necessary to prevent the solid matters of α-SF salt from consolidating with each other and forming cakes.

SUMMARY OF THE INVENTION

Technical Problem

Accordingly, a first object of the invention is to provide an α-SF salt with improved anti-caking properties.

Another object of the invention is to provide a detergent composition comprising an α-SF salt with improved anti-caking properties.

Further object of the invention is to provide a method for producing an α-SF salt with improved anti-caking properties.

Solution to Problem

As a result of intensive studies, the inventors of the present invention found that a particular treatment can convert the α-SF salt into a novel crystalline state with a stable structure that is difficult to cake. When the α-SF salt in the above-mentioned stable crystalline state is allowed to exist together with the α-SF salt in a metastable crystalline state in a specified ratio, the resultant effects are found to be similar to those obtainable in the case where the α-SF salt in a stable crystalline state exists alone.

Accordingly, the invention provides a fatty acid alkyl ester sulfonate metal salt mixture consisting of;

(a) a fatty acid alkyl ester sulfonate metal salt having an endothermic peak area at 50 to 130° C. of less than 50% relative to the whole endothermic peak area at 0 to 130° C. as measured on a differential scanning calorimeter, and (b) a fatty acid alkyl ester sulfonate metal salt having an endothermic peak area at 50 to 130° C. of 50% or more relative to the whole endothermic peak area at 0 to 130° C. as measured on a differential scanning calorimeter, with a ratio of (a) to (b) by mass of 95/5 or less.

The invention also provides a detergent composition comprising the above-mentioned fatty acid alkyl ester sulfonate metal salt mixture.

Further, the invention provides a method for producing a fatty acid alkyl ester sulfonate metal salt powder mixture, comprising the steps of:

mixing (a) a fatty acid alkyl ester sulfonate metal salt having an endothermic peak area at 50 to 130° C. of less than 50% relative to the whole endothermic peak area at 0 to 130° C. as measured on a differential scanning calorimeter, and (b) a fatty acid alkyl ester sulfonate metal salt having an endothermic peak area at 50 to 130° C. of 50% or more relative to the whole endothermic peak area at 0 to 130° C. as measured on a differential scanning calorimeter, and pulverizing the mixture to obtain the fatty acid alkyl ester sulfonate metal salt powder mixture with a ratio of (a) to (b) by mass of 95/5 or less, wherein the mixing step and the pulverizing step may be carried out in the reverse order.

According to the invention, it is possible to obtain the α-SF salt with improved anti-caking properties. The α-SF salt according to the invention also shows excellent fluidity.

BRIEF DESCRIPTION OF THE DRAWINGS

FIG. 3-1 is a diagram showing the DSC peaks of a crystalline MES obtained by allowing the metastable solid MES with a water content of 1.9% to stand at 35° C. for 4 weeks; and FIG. 3-2 is a diagram showing the DSC peaks of a crystalline MES obtained by allowing the metastable solid MES with a water content of 3.3% to stand at 35° C. for 4 weeks.

FIG. 4 is a schematic diagram showing the baseline used as the reference for calculating the endotherm and explaining the way of splitting the peak.

DETAILED DESCRIPTION OF THE INVENTION

[α-SF Salt]

Figure 1:
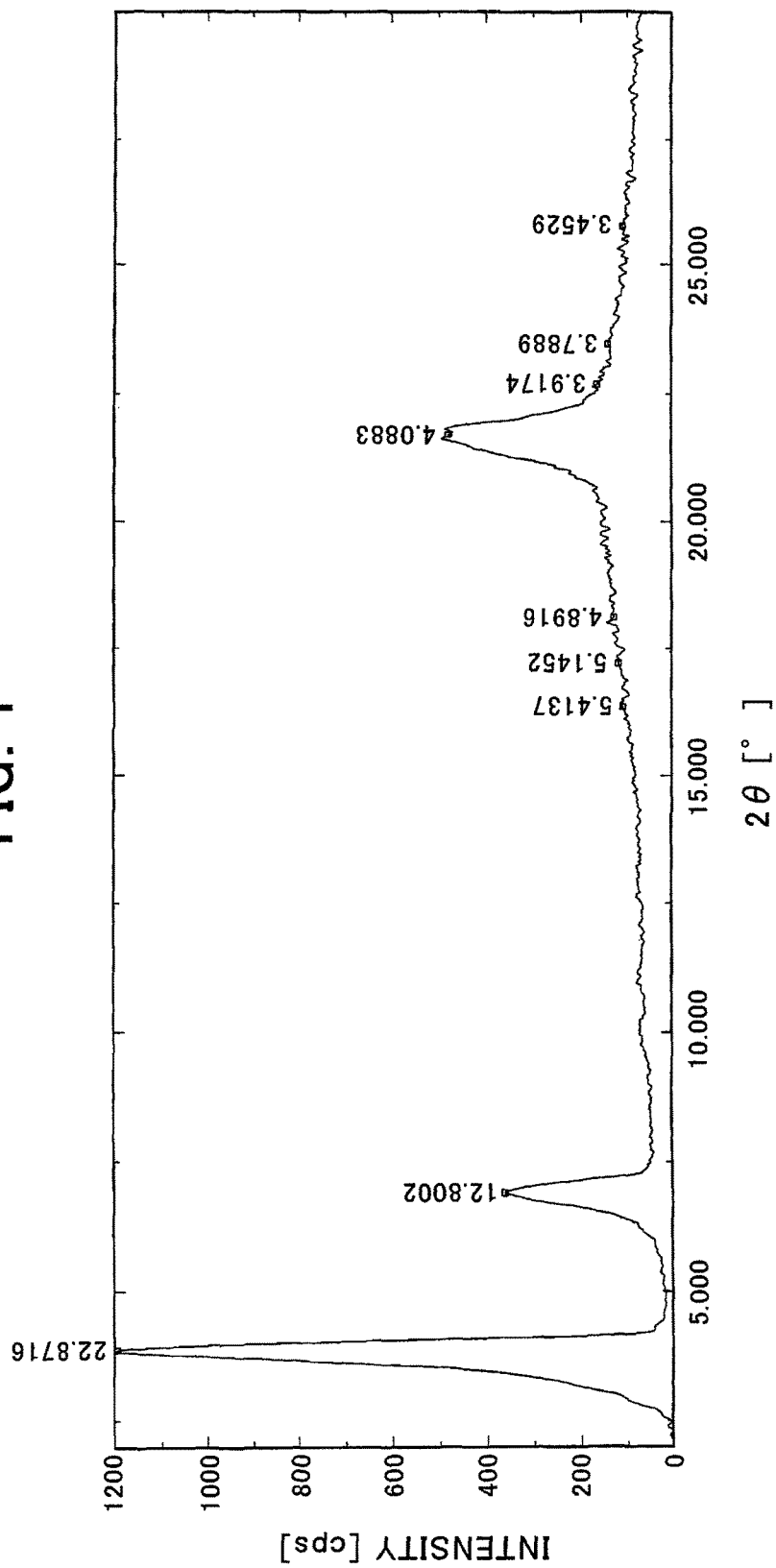
FIG. 1 is a diagram showing the X-ray diffraction peaks of a metastable solid MES.

The α-SF salt is represented by the following formula (1):

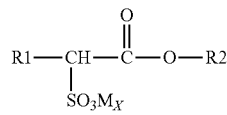

(1)

In the formula (1), $R^1$ is a straight-chain or branched alkyl or alkenyl group having 10 to 20 carbon atoms, preferably 10 to 18 carbon atoms, and more preferably 10 to 16 carbon atoms; $R^2$ is a straight-chain or branched alkyl group having 1 to 4 carbon atoms, preferably 1 to 2 carbon atoms; M is an alkali metal ion or alkaline earth metal ion, preferably an alkali metal ion, and more preferably sodium or potassium; and X is 1 when M is an alkali metal ion, and ½ when M is an alkaline earth metal ion.

In the invention, one kind of MES may be used alone, or two or more kinds may be used as a mixture. The latter is preferable. More preferably, the mixture may contain a compound represented by the above-mentioned formula (1) wherein $R^1$ represents a straight-chain or branched alkyl group or alkenyl group having 14 or 16 carbon atoms.

The fatty acid alkyl ester sulfonate metal salt mentioned above may be prepared by the conventional methods, or commercially available products may be used.

The α-SF salt is known to assume a variety of crystalline states. For example, 2-sulfopalmitic acid methyl ester sodium salt assumes stable crystalline states, such as anhydrous crystalline state, crystalline dihydrate, crystalline pentahydrate, and crystalline decahydrate. According to the report, the melting point of the anhydride is 112° C., and that of the above-mentioned dihydrate is 70° C. (M. Fujiwara, et. al., Langmuir, 13, 3345 (1997)).

[Metastable Solid (a) of α-SF Salt]

The metastable solid α-SF salt herein used means the solid α-SF salt having an endothermic peak area (A) at 50 to 130° C. of less than 50% relative to the whole endothermic peak area (B) at 0 to 130° C. as measured on a differential scanning calorimeter. The ratio of the above-mentioned endothermic peak area (A) to the whole endothermic peak area (B) may preferably be 40% or less, more preferably 30% or less.

The metastable solid α-SF salt can be obtained by rapidly cooling the melted α-SF salt. The α-SF salt in any crystalline state may be used. For example, when the α-SF salt is melted at temperatures between 100° C. and 150° C. and then cooled to 0 to 40° C. three minutes or fewer after melting, the metastable solid α-SF salt can be obtained.

The metastable solid is supposed to be a solid formed by supercooling the liquid crystal. The metastable solid α-SF salt is characterized by having a crystalline structure with three diffraction peaks respectively having peak tops between the lattice spacings of 20 and 30 Å, 10 and 15 Å, and 3 and 5 Å when determined by X-ray diffraction (FIG. 1).

Such a metastable solid state cannot easily be formed from a pure α-SF salt. The metastable solid state can be formed easily when side products such as methyl sulfate metal salt and fatty acid sulfonate metal salt are contained in the α-SF salt. The methyl sulfate metal salt can decrease the viscosity of the α-SF salt in a paste form, thereby improving the handling properties. The metastable solid is considered to be an advantageous state in terms of the manufacturing process because the solid state can be readily formed by rapid cooling. The methyl sulfate metal salt is represented by the following formula (2). The fatty acid sulfonate metal salt is represented by the following formula (3) or (4).

(2)

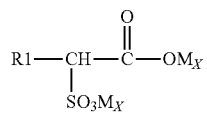

(3)

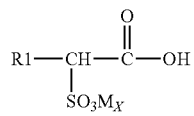

(4)

In the formula (2), $R^3$ is a straight-chain or branched alkyl group having 1 to 4 carbon atoms; and M and X are the same as those previously defined.

In the formulas (3) and (4), $R^1$, M and X are the same as those previously defined in formula (1).

Preferably, the metastable solid α-SF salt may be prepared from 60 to 98 mass % of a fatty acid alkyl ester sulfonate metal salt, 1 to 10 mass % of an alkyl sulfate metal salt, and 1 to 10 mass % of a fatty acid sulfonate metal salt. When the content of the α-SF salt is less than 60 mass %, the physical properties of the resultant solid may be more influenced by other materials than the α-SF salt. When the content of the α-SF salt exceeds 98 mass %, the physical properties of the resultant solid may considerably vary to worsen the handling properties during the production. When the content of the alkyl sulfate metal salt or the fatty acid sulfonate metal salt exceeds 10 mass %, the rate at which the metastable solid α-SF salt is converted into a stable crystal form is significantly decreased. Particularly, a compound represented by formula (1) wherein $R^1$ is a straight-chain or branched alkyl or alkenyl group having 14 carbon atoms may be contained in an amount of 40 mass % or more, preferably 60 mass % or more, and more preferably 80 mass % or more of the total mass of the fatty acid alkyl ester sulfonate metal salt.

[Stable Solid (b) of α-SF Salt]

The stable solid α-SF salt herein used means the solid α-SF salt having an endothermic peak area at 50 to 130° C. of 50% or more relative to the whole endothermic peak area at 0 to 130° C. as measured on a differential scanning calorimeter. The ratio of the above-mentioned endothermic peak area (A) to the whole endothermic peak area (B) may preferably be 70% or more, and more preferably 80% or more.

Even though the stable solid α-SF salt is allowed to exist together with the α-SF salt in any other states than stable solid state, the amount of solid to be melted can be decreased under the circumstances of high temperatures, for example 40° C. or more. As a result, the adhesion properties caused by the metastable solid MES can be controlled, thereby reducing the caking tendency.

In the invention, the fatty acid alkyl ester sulfonate metal salt can exhibit improved anti-caking properties by adding the above-mentioned stable solid (b) to the metastable solid (a) in a particular ratio. The ratio of (a) to (b), i.e., (a)/(b), is 95/5 or less, preferably 80/20 or less, more preferably 75/25 or less, and further preferably 70/30 or less.

From the viewpoint of fluidity, the lower limit of the (a)/(b) ratio is preferably 5/95 or more, more preferably 20/80 or more, and further preferably 25/75 or more.

The residue of fatty acid for constituting the above-mentioned metastable solid (a) and that for the above-mentioned stable solid (b) may have the same or different number of carbon atoms.

The stable solid α-SF salt may be prepared, for example, according to any of the following methods (I) to (III).

(I) The metastable solid α-SF salt is maintained at 30° C. or more for at least 48 hours under pressure of 20,000 Pa or less.

(II) The metastable solid α-SF salt is melted and the obtained melt is maintained for 5 minutes or more at temperatures between the melting point of the above-mentioned metastable solid metal salt and the melting point of the above-mentioned stable solid.

(III) The metastable solid α-SF salt is melted and a shearing force is applied to the obtained melt at a shear rate of 100 (1/s) or more at temperatures between the melting point of the above-mentioned metastable solid metal salt and 80° C.

The conversion of the α-SF salt into a stable solid state or crystallize the α-SF salt will also be referred to as "aging".

<Method (I) for Converting into Stable Solid>

When maintained at temperatures of less than 30° C., the metastable solid α-SF salt can convert into the stable solid state, but extremely slowly. Therefore, to maintain the metastable solid at 40° C. or less is desirable. When maintained at temperatures of more than 40° C., the metastable solid is found to slightly melt, and therefore, the metastable solid α-SF salt unfavorably tends to fuse to each other, which may form cakes during the storage. The temperature at which the metastable solid is maintained is not necessarily required to be constant as long as it is 30° C. or more. For example, intermittent heating and cooling is allowable. The way of setting the temperature is not particularly limited. For example, after the α-SF salt is placed into a container, the external environment of the container may be adjusted to the specified temperature. Alternatively, the container itself may be controlled to the specified temperature, or airflow of the specified temperature may be blown into the container. It is possible to use as the container, a silo, flexible container bag, drum, craft paper bag, polyethylene bag or the like.

A pressure over 20,000 Pa may cause caking while maintaining. Practically, while the α-SF salt is filled into the container for storage, due to the weight of α-SF salt itself, pressure will inevitably be exerted especially on the bottom part of the container. The pressure herein used means a pressure to be exerted on the bottom surface, which is defined by the following formula: pressure (Pa)=mass (kg) packed in a container×acceleration of gravity g (m/s$^2$)/area of base (m$^2$) of the container. To maintain the metastable solid α-SF salt under 12,000 Pa or less is desirable. It is further preferable to maintain the metastable solid α-SF salt under the application of 500 to 8,000 Pa.

When the maintaining time is less than 48 hours, the conversion from the metastable solid to the crystal form may become insufficient. The maintaining time is six weeks at the longest, preferably 72 hours or more.

While the α-SF salt is maintained under the above-mentioned conditions, the container holding the α-SF salt therein may be tightly sealed or left open. When the container is left open, the contact with damp air should be avoided in consideration of the effects of moisture absorption.

In particular, it is preferable to maintain at 30 to 35° C. and 3,000 to 7,000 Pa for 200 to 400 hours.

The melting point of the obtainable stable solid α-SF salt is as high as 50° C. or more, so that the solid material is not easily melted even when stored at high temperatures.

<Method (II) for Converting into Stable Solid>

The temperature of the above-mentioned process (II) can be determined from the melting points of the metastable solid and the crystal. The melting points of the metastable solid and the crystal may be obtained in advance using a differential scanning calorimeter (DSC).

For example, when the α-SF salt represented by the above-mentioned formula (1) is used as the raw material, the melt is preferably maintained at temperatures of 40° C. or more and less than 90° C., more preferably 50° C. or more and less than 80° C. When the temperature is not within the above-mentioned range, it may become difficult to form a crystal form in a short time. In addition, when the maintaining time is less than 5 minutes, the solid material may not reach such a stable state as specified by the DSC. In particular, the melt may be preferably maintained at 55 to 75° C. for 10 to 500 minutes.

<Method (III) for Converting into Stable Solid>

According to the above-mentioned method (II), a solid α-SF salt can be obtained by allowing the melt of α-SF salt to stand at a predetermined temperature for a given time. In the method (III), a shearing force is applied to the melt instead of leaving the melt standing for a given time. The application of a shearing force can accelerate the conversion into the crystal form.

The means for applying a shearing force is not particularly limited, and for example, a variety of kneaders and extrusion granulators may be used. To be more specific, the commercially available apparatus such as KRC kneader made by Kurimoto, Ltd., Milling Prodder made by Mazzoni S.p.a and the like can be used.

The shear rate is defined by dividing the impeller tip speed by clearance. Preferably, the shear rate may be 100 (1/s) or more, more preferably 150 (1/s) or more. When the shear rate is less than 100 (1/s), the agitation performance may be insufficient to make the solid material into such a stable state as specified by the DSC.

Preferably, the shearing operation may be carried out for five seconds or more and less than five minutes. With the shearing time of less than five seconds, it is hard to obtain a stable solid material. To carry out the shearing operation for more than five minutes, extremely large-scale apparatus will be needed. Particularly, the shearing force may be applied at a shear rate of 200 to 5,000 (1/s) at 55 to 75° C.

[DSC Peaks of the Stable Solid and Metastable Solid]

Figure 2:
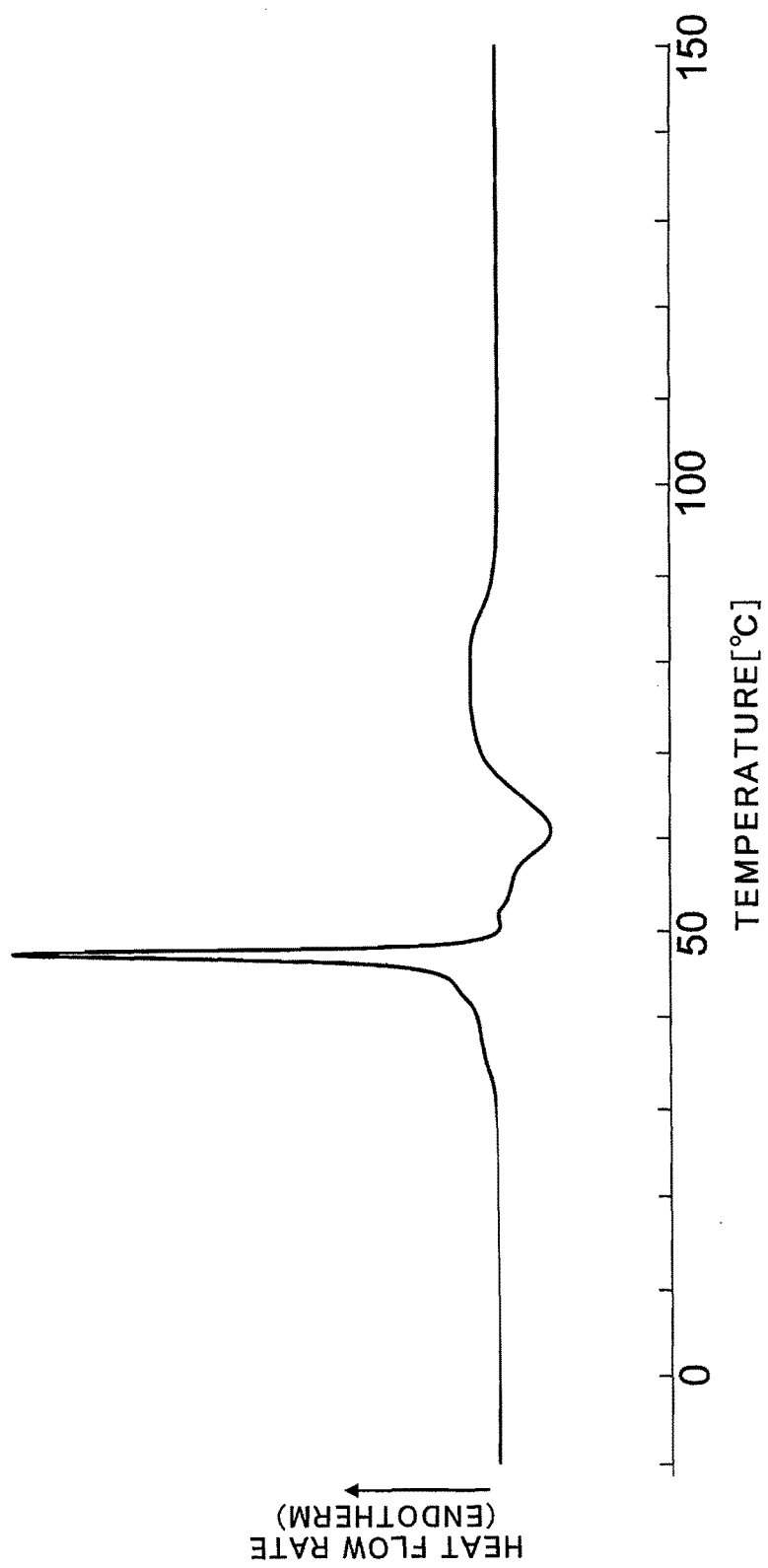
FIG. 2 is a diagram showing the DSC peaks of a metastable solid MES.
Figures 1, 6:
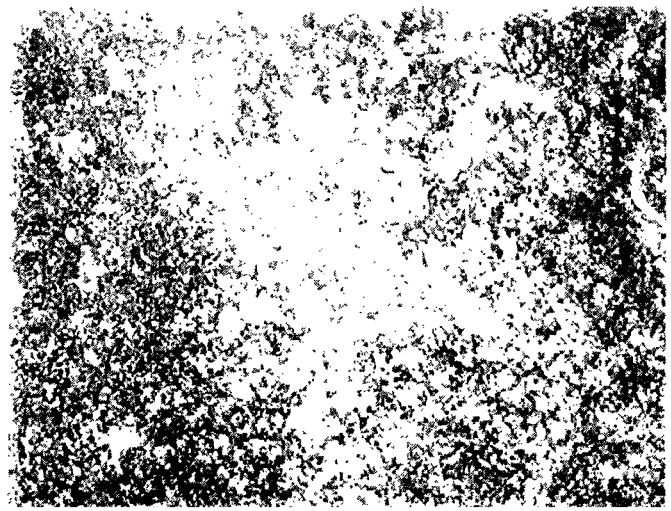
FIG. 6 is a series of microscope photographs showing a crystalline MES included in the invention. The height of the microscope photograph corresponds to 750 μm and the width thereof corresponds to 1000 μm.
Figures 2, 6:
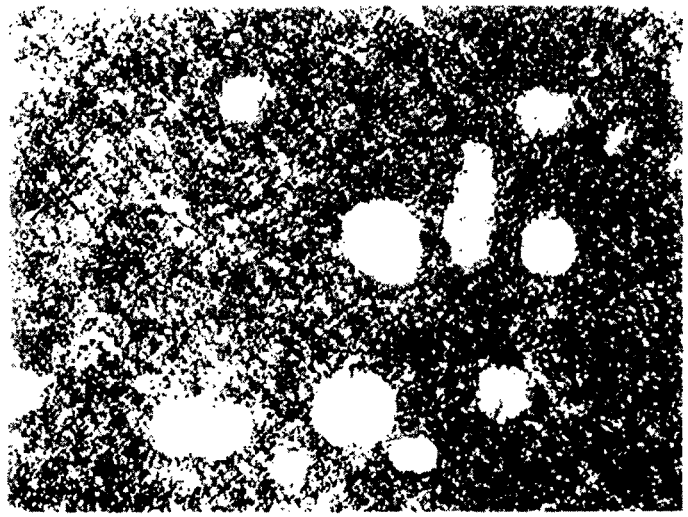
Figures 3, 6:
FIG. 3 shows the DSC peaks of a crystalline MES (stable solid MES) included in the invention.

The DSC peaks of the crystalline α-SF salt are different from those of the metastable solid α-SF salt, which will be explained by referring to the MES prepared from a mixture of two compounds of formula (1) wherein $R^1$ has respectively 14 carbon atoms and 16 carbon atoms. The endothermic peak appears between about 35° C. and about 55° C. according to the DSC of the metastable solid, which shows the melting peak having a peak top between about 40° C. and about 50° C. (FIG. 2). In contrast to this, the endothermic peak is observed over about 50° C. in the DSC of the crystalline MES (FIG. 3). When FIG. 3 is compared with FIG. 2, the MES having a crystal structure has less peaks around 40 to 50° C. as shown in FIG. 3 and is said to be more stable over the higher temperature range, in contrast to the metastable solid MES as shown in FIG. 2. Further, in the crystalline MES a plurality of peaks appearing between about 50° C. and about 70° C. and between about 70° C. and about 90° C. are observed as the endothermic peaks, and the absolute value of the latter endothermic peak is higher when the water content is lower (FIG. 3-1 and FIG. 3-2).

The ratio of A to B as specified by the invention is determined by placing a sample for analysis into an aluminum pan or stainless steel pan and measuring the endotherm and exotherm at a predetermined heating rate using a differential scanning calorimeter. Under certain circumstances, exothermic peaks may be observed at temperatures of 100° C. or less. In this case, the value A is obtained by subtracting the exotherm from the endotherm over 50° C. Similarly, for the value B, a total endotherm is obtained by subtracting the absolute value of exotherm of the exothermic peaks from the endotherm of the endothermic peaks.

The endotherm is calculated with reference to a baseline, which is defined by the straight line obtained by joining straight-line segments before and after the endothermic peak.

By referring to a diagram shown in FIG. 4, those skilled in the art could easily understand how to determine the baseline and how to split the peak.

The melting point is defined by a peak top value. For example, the melting point of the metastable solid is defined by a peak top of the peak appearing around temperatures of 50° C. or less, as shown in FIG. 2. The melting point of the crystalline MES solid is defined as a temperature corresponding to a peak top of the peak appearing in a higher temperature region, that is, between 50° C. and 130° C. Specifically, the peak in FIG. 3-1 and the peak of the higher temperature region in FIG. 3-2 are respectively 88° C. and 78° C. The melting point of the crystalline MES solid varies depending on the water content and other components contained in the MES. With the conversion from the metastable solid to the crystal form of MES, the peak in the higher temperature region is shifted. Also, to determine the melting point of the crystalline MES, the same measurement by the DSC is carried out using a cell holding therein an appropriate sample. The melting point of the crystalline MES is regarded as the temperature corresponding to the peak top of a peak appearing at the highest temperature among the peaks of which intensities are 10% or more relative to that of the maximum peak. If the melting point is not definite, the measurement may be conducted after the sample is stored at 45° C. for one week. This process can clearly determine the melting point.

As for the differential scanning calorimeter, any commercially available differential scanning calorimeters, including power-compensation type and heat-flux type can be used. For example, the commercially available calorimeters such as Diamond DSC (Perkin Elmer Inc.), EXSTAR 6000 (Seiko Instruments Inc.) and the like can be used. As the sample pan, a silver pan, aluminum pan or stainless steel pan is used. The heating rate is preferably 1 to 2° C./min. When the heating rate is slower than the above-mentioned rate, the noise will increase. When the heating rate becomes more rapid, detection of minute peaks may become impossible.

Figure 5:
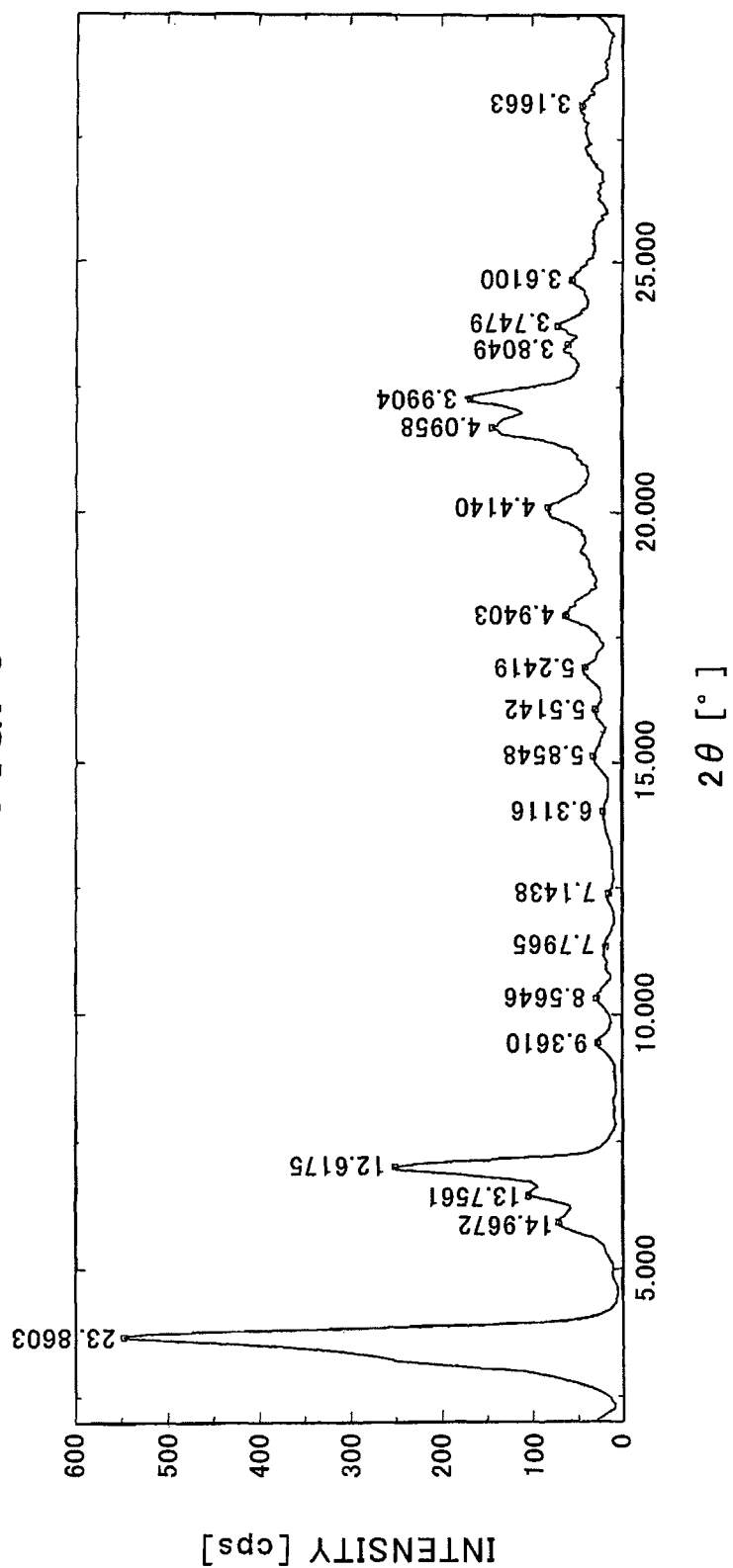
FIG. 5 is a diagram showing X-ray diffraction peaks of a crystalline MES included in the invention.

When the crystalline MES is subjected to X-ray diffraction, many reflections probably resulting from the crystal lattice are detected (FIG. 5). In light of this, the crystalline MES is considered to form a molecular crystal with a general Bravais lattice. It would be easy to distinguish whether the MES assumes the crystal form or the metastable solid state because the X-ray diffraction (FIG. 1) of the metastable solid MES showing three broad reflection peaks is apparently different from that of the crystalline MES.

It is also possible to observe the crystalline α-SF salt using a microscope, although it depends on the crystal growing process. When the MES in a metastable state is melted, followed by rapid cooling, a solid phase with a homogeneous polarization is observed as shown in FIG. 6-1. When the MES is melted and then allowed to stand at 60° C., the crystals are growing and needle crystals are then observed (FIG. 6-2), and at last the needle crystals become predominant (FIG. 6-3). The crystals may grow concentrically, with the seed crystal as the central point as shown in this figure, or the needle crystals may homogeneously grow.

The results of the DSC, X-ray diffraction and microscopic observation can demonstrate that the crystalline MES is distinctly different from the known metastable MES in the physicochemical condition. It is also said that the presence of the crystal form can be recognized by the DSC and the X-ray diffraction.

The crystalline α-SF salt according to the invention may preferably have a water content of 10% or less, more preferably 5% or less. When the water content exceeds 10%, the preservation stability of the crystalline α-SF salt according to the invention will tend to deteriorate. This will increase the adhesion properties at low temperatures, and therefore the degree of improvement in storage properties and transportability may drastically decrease. The lower limit is preferably 0.5% or more.

[α-SF Salt Mixture]

The α-SF salt mixture according to the invention may be used in various forms, preferably in the form of flakes or particles. The particles can assume various forms such as powders, pellets, noodles, ground products thereof, and the like. Preferably, the stable solid and the metastable solid may be both in the form of powders, having almost the same particle diameters.

When the α-SF salt of the invention is in the form of flakes or particles, the mean particle diameter, which will be defined later, may preferably be at least 3 mm, more preferably 5 mm or more and 100 mm or less. When the mean particle diameter is less than 3 mm, the number of contact points and the contact area increase, so that the particles cannot withstand the increased adhesion between the particle surfaces to readily tend to induce caking with the increase of temperature. In the case where the mean particle diameter is supposed to be 3 mm or more, the mean particle diameter is determined by the following method. The axis having a maximum length of a flake or particle is supposed to be X; the axis of a cross section having a maximum length, perpendicular to the axis X is supposed to be Y; the axis perpendicular to the two axes X and Y is supposed to be Z. The diameter obtained by averaging the total of the maximum length of X, the maximum length of Y and the length of Z axis is regarded as a characteristic diameter of one particle. The characteristic diameters of 50 or more flakes or particles are measured and the weight average particle diameter is obtained. With respect to the flakes or particles including those with a particle diameter of less than 3 mm, the flakes or particles are subjected to dry-sieving according to JIS Z8815 and the percentage of cumulative undersize distribution is plotted on the Rosin-Rammler's chart. The mean particle diameter is regarded as that indicating the percentage of 50%, which is added to the percentage to be described later as the weight average value.

The pellets and noodles can be produced in such a manner that the melted fatty acid alkyl ester sulfonate metal salt-containing product or flakes are charged into an extrusion granulator or kneader and then passed through a die or the like having an appropriate diameter. Examples of the extrusion granulator include Pelleter Double and Twin Dome Granulator, made by Fuji Paudal Co., Ltd., and Gear Pelletizer and Extrud-O-Mix, made by Hosokawa Micron Corporation.

When the melted fatty acid alkyl ester sulfonate metal salt-containing product is cooled, it will assume a solid state. In the course of cooling, the melt is formed into a plate-shaped solid using a drum flaker, belt cooler or the like, and then crushed, thereby obtaining flakes. Examples of the flaker include Drum Flaker made by Katsuragi Industry. Co., Ltd., and Drum Flaker FL made by Mitsubishi Materials Corporation. Examples of the belt cooler include Double Belt Cooler and NR type Double Belt Cooler made by Nippon Belting Co., Ltd., and a double belt cooling system made by Sandvik Materials Technology. As the crusher, for example, Flake Crusher FC made by Hosokawa Micron Corporation or the like can be used.

The particles (powders) of $\alpha$-SF salt mixture can be prepared by crushing the flakes, pellets, noodles or the like using a pulverizer. Examples of the pulverizer include a hammer mill, a pin mill and the like. As the hammer mill, Feather Mill FS made by Hosokawa Micron Corporation and Fitzmill made by Fitzpatrick Company can be used. The flakes of metastable solid (b) and the flakes of stable solid (a) as previously mentioned may be charged into a pulverizer to obtain a mixture of powders in the pulverizer. Alternatively, the flakes of metastable solid (a) and the flakes of stable solid (b) may be separately pulverized using pulverizers before blending to obtain a mixture.

The $\alpha$-SF salt mixture according to the invention contains the crystalline $\alpha$-SF salt. Accordingly, even though the mixture is subjected to pulverizing, adhesion to the pulverizer can be reduced. In addition, the pulverizing operation can be carried out at high temperatures, so that it becomes possible to obtain $\alpha$-SF salt powders with a sharp particle size distribution. In this case, the same pulverizers as can be used in the preparation of the crystalline $\alpha$-SF salt are usable.

In the course of pulverizing, the internal temperature of the pulverizer is not particularly limited, but preferably 30° C. or more and 50° C. or less, more preferably 30° C. or more and 40° C. or less, and most preferably 33° C. or more and 38° C. or less. When the internal temperature is less than 30° C., the particle size distribution of the obtainable powder becomes broad and the amount of fine particles may increase. When the internal temperature exceeds 50° C., some powders may adhere to the pulverizer because of the increased adhesion of the powders.

Although the temperature of the inside of the pulverizer is not particularly limited, the temperature may be controlled by adjusting the temperature of airflow in the case where the airflow is blown into the pulverizer in the course of pulverizing. Alternatively, even if the airflow is not blown into the pulverizer, the internal temperature of the pulverizer may be controlled by adjusting the temperature of flakes or maintaining the external temperature of the pulverizer. The inside of the pulverizer herein used means the inner part of the container enclosing and holding a portion where the blade, hammer or the like is driven to actually pulverize the flakes or the like.

In particular, pulverizing may be carried out, with a screen been provided. The screen with a pore diameter of 2 mm is used when the increase of coarse particles is expected; and the screen with a pore diameter of 3 mm is used when the increase of fine particles is expected. As a matter of course, the obtained particle size becomes larger by using the screen with larger pores; and smaller by using the screen with smaller pores.

The inventors found that the amount of coarse powders can especially be reduced by increasing the number of revolutions (i.e., peripheral speed) in the pulverizing operation. It is preferable to carry out the pulverizing operation at 200 to 8000 rpm, more preferably 600 to 5000 rpm. The particle size tends to decrease with the increase of the number of revolutions, while the particle size tends to increase with the decrease of the number of revolutions. The peripheral speed (i.e., the peripheral speed of rotary blade tips) may be preferably in the range of 20 to 70 m/s, more preferably 30 to 60 m/s, and most preferably 35 to 55 m/s.

The pulverizing time is generally from five seconds to five minutes.

The multiple-stage pulverizer can be used where pulverizing units are arranged in series or in parallel.

The powders of $\alpha$-SF salt mixture according to the invention can also be obtained by subjecting the above-mentioned stable solid (a) and metastable solid (b) to the conventional agitation granulation method or kneading-crushing granulation method.

Particularly, when the kneading-crushing granulation method is employed, it is advantageous to carry out the granulation process with the addition of inorganic powders to be described later in consideration of the solubility of the obtainable powders of $\alpha$-SF salt mixture. As the inorganic powder, zeolite is preferably used. Use of the above-mentioned stable solid (a) and metastable solid (b) can weaken the adhesion of the surface of extruded product immediately after kneading and extrusion, and therefor coalescence of the extruded product can be prevented. This will lead to effective cooling operation to upgrade the production capacity.

When the powders of $\alpha$-SF salt mixture according to the invention are obtained by the agitation granulation method or kneading-crushing granulation method, the ratio (by mass) of the stable solid (a) to the metastable solid (b) in the obtained powders of $\alpha$-SF salt mixture may become larger than the ratio (by mass) of the stable solid (a) to the metastable solid (b) before mixing. Without wishing to be bound by any theory, the metastable solid is supposed to be converted into stable solid when energy generated by the agitation granulation or kneading-crushing granulation is applied to the metastable solid, and therefore the amount of stable solid is supposed to increase. The ratio of the stable solid (a) to the metastable solid (b) in the obtained powders of $\alpha$-SF salt mixture can be set within the range as specified by the invention by appropriately controlling the conditions of agitation granulation or kneading-crushing granulation, including the temperature, time and the like. When the kneading-crushing granulation method is employed, the application of a shearing force at a shear rate as mentioned in the section of <Method (III) for converting into stable solid> is preferable. In particular, the shearing force may preferably be applied at a shear rate of 200 to 5000 (l/s) at 55 to 75° C. The ratio of the stable solid (a) to the metastable solid (b) in the mixture can be determined using the differential scanning calorimeter as mentioned above.

According to the particle size distribution of the $\alpha$-SF salt powder mixture of the invention, the fraction of "1000 μm on" may preferably be 50 mass % or less, more preferably 8 mass % or less; and the fraction of "149 μm pass" may preferably be 10 mass % or less, more preferably 8 mass % or less. The above-mentioned particle size distribution is advantageous in terms of the solubility. The particle size distribution can be determined in the same manner as described below in the mass frequency percent.

When any coating is not applied to the powders, the α-SF salt powder mixture according to the invention may preferably have a mean particle diameter of 300 to 3000 μm, more preferably 400 to 600 μm. The mean particle diameter within the above-mentioned range is advantageous in terms of the solubility.

The α-SF salt powder mixture according to the invention may preferably have a bulk density of 0.55 to 0.75 kg/L, more preferably 0.60 to 0.70 kg/L. The bulk density within the above-mentioned range is preferred because of the advantages of space-saving and good solubility. The bulk density can be determined in accordance with the JIS K 3362: 1998.

In the course of production of the α-SF salt powder mixture according to the invention, the pulverizing step may be carried out with the addition of inorganic powder. Any inorganic powder that is generally used for the production of granular detergent compositions can be employed with no restrictions. The inorganic powder with a mean particle diameter of 0.1 to 100 μm, preferably 0.5 to 50 μm, and more preferably 0.5 to 30 μm may be used. When the mean particle diameter of the inorganic powder is less than 0.1 μm, the dusting properties may worsen in some cases. With the mean particle diameter of more than 100 μm, the mixed powder may become heterogeneous by size separation during the storage time.

The mean particle diameter of the inorganic powder can be determined using a laser diffraction/scattering type particle size analyzer, for example, Partica LA-950V2, made by Horiba, Ltd., LDSA-1400A made by Tohnichi Computer Applications Co., Ltd., or the like.

The inorganic powder may be mixed in an amount of 30 mass % or less, preferably 1 to 20 mass %, and more preferably 5 to 10 mass %, based on the total mass of the finished product. In this case, addition of inorganic powder is effective for upgrading the physical properties of the α-SF salt powder. The inorganic powder, which may not be necessarily mixed with the α-SF salt powder, would still more effectively contribute to the prevention of caking of the powder during the long-term storage when added. When the amount of inorganic powder exceeds 30 mass %, there occurs a problem in fluidity of the mixture powder.

The inorganic powder may be fed into the pulverizer before the flakes or pellets are subjected to pulverizing, or during or after the pulverization of the flakes or pellets. To mix the inorganic powder with the flakes or pellets or ground powders, any apparatus designed for dry blending can be used with no limitation. Specific examples of the apparatus include a horizontal drum-shaped blender, V-shaped mixer, and agitating granulator, which are considered as illustrative and not restrictive.

The caking tendency of the α-SF salt powders can be further reduced by applying a coating onto the α-SF salt powders.

The coating agent includes inorganic powders and powders of organic acid salts and the like, which may be water-soluble or not. One kind of coating agent may be used alone or two or more kinds may be appropriately used in combination. Examples of the inorganic powders include aluminosilicates such as zeolite A, sodium carbonate, alkaline earth metal salt carbonates such as calcium carbonate and magnesium carbonate, amorphous silica, white carbon (silica), silicates such as sodium silicate, calcium silicate, magnesium silicate and the like, clay minerals such as talc, bentonite and the like, silicon dioxide, titanium dioxide, finely-divided particles of sodium carbonate, sodium sulfate, potassium sulfate, sodium tripolyphosphate and the like. In particular, aluminosilicate, sodium carbonate and sodium sulfate are preferable. Examples of the organic acid salts include metallic soap such as stearates, sodium acetate, sodium citrate and the like. In particular, stearates are preferred.

The finely ground product of metastable solid α-SF salt tends to cake under high temperatures even though the finely ground product is covered with the coating agent as mentioned above.

The amount of the coating agent is preferably 1 to 30 mass %, more preferably 1 to 20 mass %, and most preferably 5 to 10 mass %, based on the mass of the α-SF salt powder. When the amount of the coating agent is less than 1 mass %, some additional effect for improving the anti-caking properties cannot be expected. When the amount of coating agent exceeds 30 mass %, the degree of freedom in formulation of other ingredients may be lowered when the coated α-SF salt powder is used in the general-purpose granular detergent compositions for clothes and granular detergent compositions for dishes.

As the coating method, the α-SF salt powder may be mixed with the coating agent, or the coating agent may be added to the flakes or particles of the crystalline α-SF salt, followed by grinding.

The mean particle diameter of the coated α-SF salt powder may be preferably 300 μm or more and 3 mm or less. When this mean particle diameter is 300 μm or more, the caking tendency can be further reduced. When the mean particle diameter of coated α-SF salt powder exceeds 3 mm, the problem of classification or the like may be produced in the case where the coated α-SF salt powder is blended into the general-purpose granular detergent compositions for clothes and dishes. This is because the particle size of the coated α-SF salt powder becomes too large among all the particles constituting the composition. The mean particle diameter is a value determined in accordance with the method shown below.

Classification is conducted using a classifier including nine sieves with the respective openings of 1680, 1410, 1190, 1000, 710, 500, 350, 250 and 149 μm, and a saucer. For the classification, above the saucer the sieves are stacked on top of each other in ascending order of opening, and 100 g of a sample of spray-dried granules is placed into the uppermost sieve of 1680 μm and the lid is closed. The classifier is set in the Ro-Tap sieve shaker (made by Iida-seisakusho Japan Corporation, 156 tappings/min, 290 rollings/min) and oscillations are applied to the classifier for 10 minutes. After that, the sample granules remaining on each sieve and the saucer are individually collected. By repeating the above-mentioned procedure, a sample classified according to the particle size, i.e., 1410 to 1680 μm (1410 μm on), 1190 to 1410 μm (1190 μm on), 1000 to 1190 μm (1000 μm on), 1000 to 710 μm (710 μm on), 500 to 710 μm (500 μm on), 350 to 500 μm (350 μm on), 250 to 350 μm (250 μm on), 149 to 250 μm (149 μm on), and the saucer to 149 μm (149 μm pass) can be obtained, and then the mass frequency percent (%) is calculated. In the above calculation, the opening of the sieve which first shows a mass frequency percent of 50% or more is supposed to be a (μm); the opening of the sieve next higher than the sieve having an opening of a (μm) is supposed to be b (μm); the cumulative finer mass frequency percent from the saucer to the sieve having an opening of a (μm) is supposed to be c (%); and the mass frequency percent on the sieve having an opening of a (μm) is supposed to be d (%). Then, the mean particle diameter (by mass-frequency percent of 50%) is determined in accordance with the following formula:

$$\text{Mean particle diameter (by mass-frequency percent of 50\%)} = 10^{(50-(c-d/\log b - \log a) \times \log b))/(d/(\log b - \log a))}$$

[Detergent Composition]

The detergent compositions for clothes and dishes can be obtained using the α-SF salt mixture according to the invention. Those detergent compositions may contain any ingredients commonly used in the detergent compositions for clothes and dishes: for example, an anionic surfactant such as straight-chain alkylbenzene sulfate metal salt, α-olefin sulfonic acid metal salt, alkylsulfate metal salt, metal salt of soap or the like; a nonionic surfactant such as alkyleneoxide adduct of higher alcohol or the like; a builder, for example, an inorganic builder such as zeolite, sodium sulfate, sodium sulfite or the like; an alkali chemical such as sodium carbonate, potassium carbonate or the like; a fluorescent agent; a bleaching agent; a bleaching activator; an enzyme; a perfume; a softening agent such as bentonite, cationic cellulose, powdered cellulose, or the like.

When contained in the detergent composition for clothes or dishes, the content of the α-SF salt mixture according to the invention (in terms of α-SF salt) is preferably 1 to 50 mass %, and more preferably 5 to 40 mass %, based on the total mass of the composition. When the α-SF salt mixture according to the invention is contained in such an amount as mentioned above, the detergent composition with higher anti-caking properties and higher fluidity can be obtained.

EXAMPLES

Preparation Example 1

[Preparation of Fatty Acid Methyl Ester Sulfonate Metal Salt (MES)]

Methyl palmitate ("PASTELL M-16", made by Lion Corporation) and methyl stearate ("PASTELL M-180" made by Lion Corporation) were mixed at a ratio of 80:20 (by mass).

In a 1-kL reaction vessel equipped with a stirrer, 330 g of the above-mentioned mixture of fatty acid methyl esters was introduced, and then anhydrous sodium sulfate was added as a coloring inhibitor in an amount of 5 mass % with respect to the above-mentioned fatty acid methyl ester mixture, with stirring. While keeping on stirring, 110 kg (equivalent to 1.1 moles to one mole of the raw material of methyl ester) of $SO_3$ gas (sulfonating gas) which was diluted to 4 vol % with nitrogen gas was blown into the mixture with bubbling at a constant rate over a period of 3 hours at the reaction temperature of 80° C. The reaction mixture was then subjected to aging for 30 minutes while maintained at 80° C.

After the reaction mixture was transferred to an esterification tank, 14 kg of methanol was added to the reaction mixture to carry out the esterification reaction at 80° C. The reaction mixture was then subjected to aging for 30 minutes while maintained at 80° C.

Then, the esterified product extracted from the reaction vessel was continuously neutralized by the addition of a sodium hydroxide aqueous solution equivalent to the esterified product using a line mixer.

Subsequently, the above-mentioned neutralized product was fed into a bleaching agent mixing line, where a 35% hydrogen peroxide solution was added in an active content of 1 to 2% with respect to the active ingredient (AI, i.e., α-sulfo fatty acid alkyl ester metal salt). The bleaching step was carried out at 80° C. with mixing, thereby obtaining a paste containing fatty acid methyl ester sulfonate metal salt.

At a feed rate of 200 kg/hour, the obtained fatty acid methyl ester sulfonate metal salt-containing paste was fed into a vacuum thin-film evaporator (made by Desmet Ballestra S.p.A, having a heat-transfer area of 4 $m^2$). The paste was concentrated at an inner wall heating temperature of 100 to 160° C. and the degree of vacuum of 0.01 to 0.03 MPa, and then a melt of 100 to 130° C. was taken out.

[Preparation of Metastable Solid MES]

Subsequently, the above-mentioned melt was cooled to 20 to 30° C. over a period of 0.5 minutes using a belt cooler (made by Nippon Belting Co., Ltd.), and then crushed using a crusher (made by Nippon Belting Co., Ltd.), to obtain flakes of metastable solid MES.

[Preparation of Stable Solid MES]

The metastable solid MES flakes were heated and turned into a melt of 60 to 63° C. The melt was placed into a KRC kneader (Model S2, made by Kurimoto, Ltd.) at a feed rate of 600 to 800 g/min and kneaded at 86 rpm for 0.5 minutes, with hot water of 51° C. flowing through the jacket of the kneader. Then, the melt taken out of the kneader was sandwiched between stainless steel plates and cooled. The cooled product was crushed with the hands to obtain stable solid flakes.

<Differential Scanning Thermal Analysis>

Figure 7:
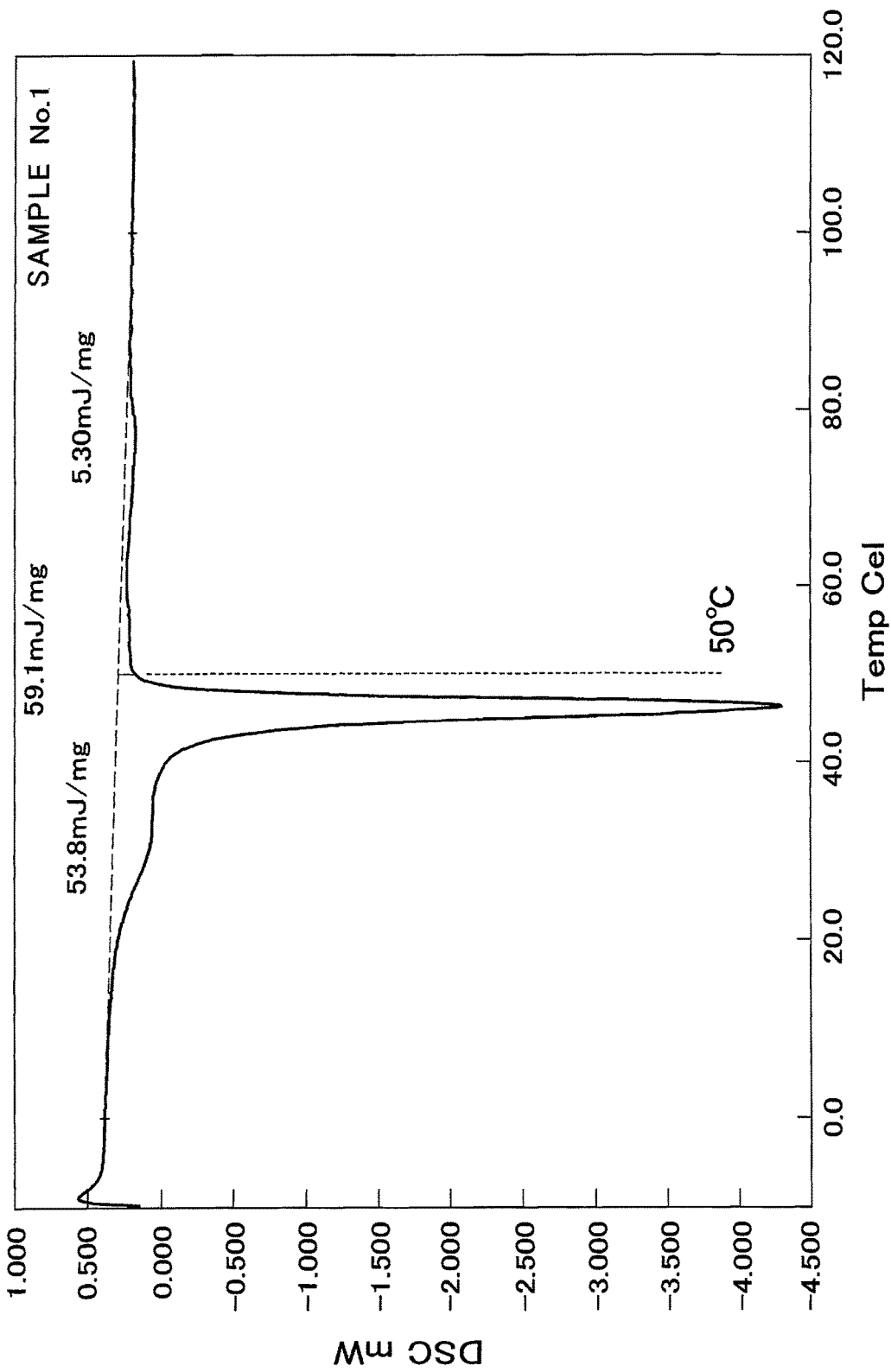
FIG. 7 is a diagram showing the DSC peaks of a metastable solid MES (sample No. 1).
Figure 8:
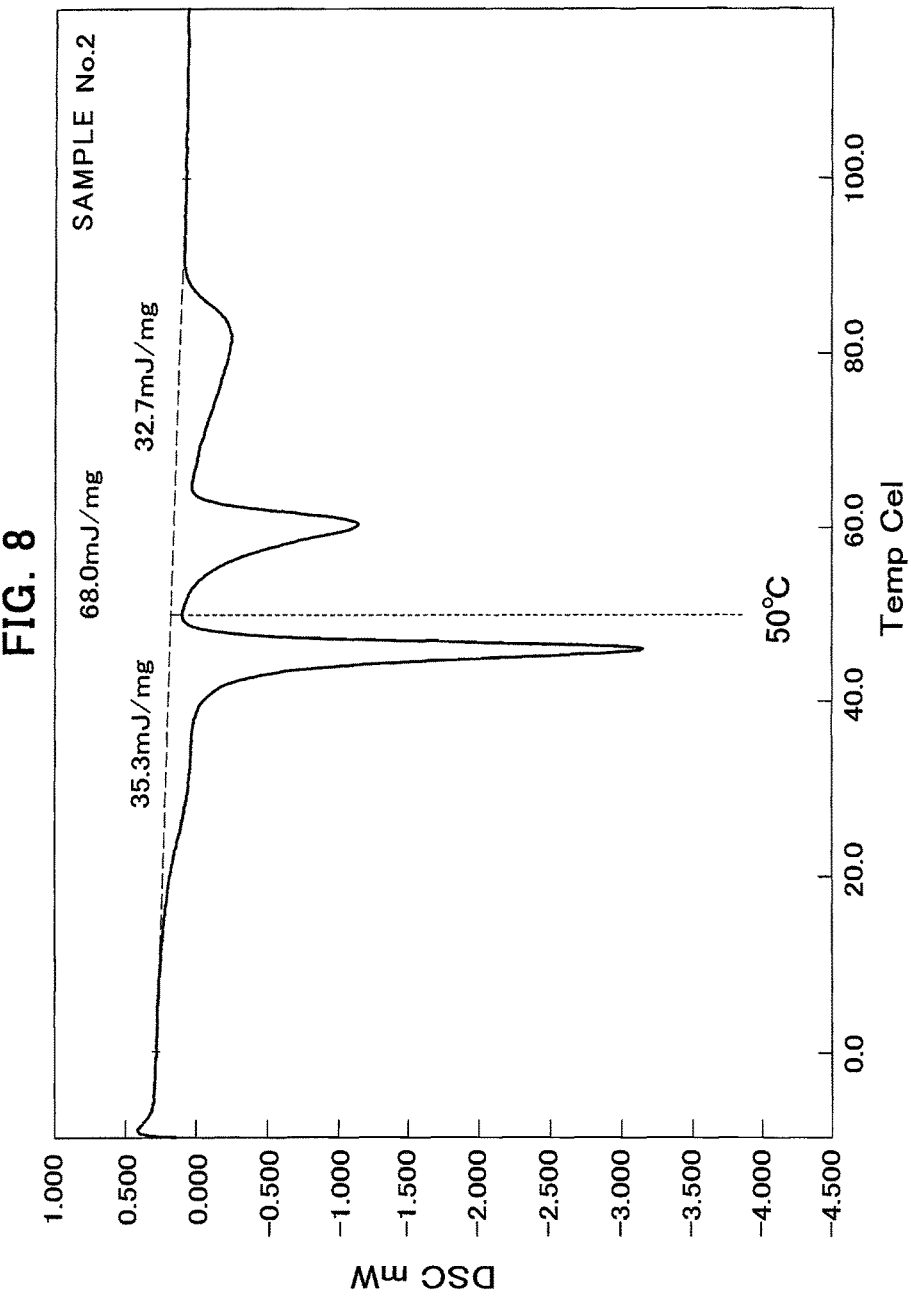
FIG. 8 is a diagram showing the DSC peaks of a mixture of a metastable solid MES and a stable solid MES (sample No. 2, metastable solid/stable solid=59/41).
Figure 9:
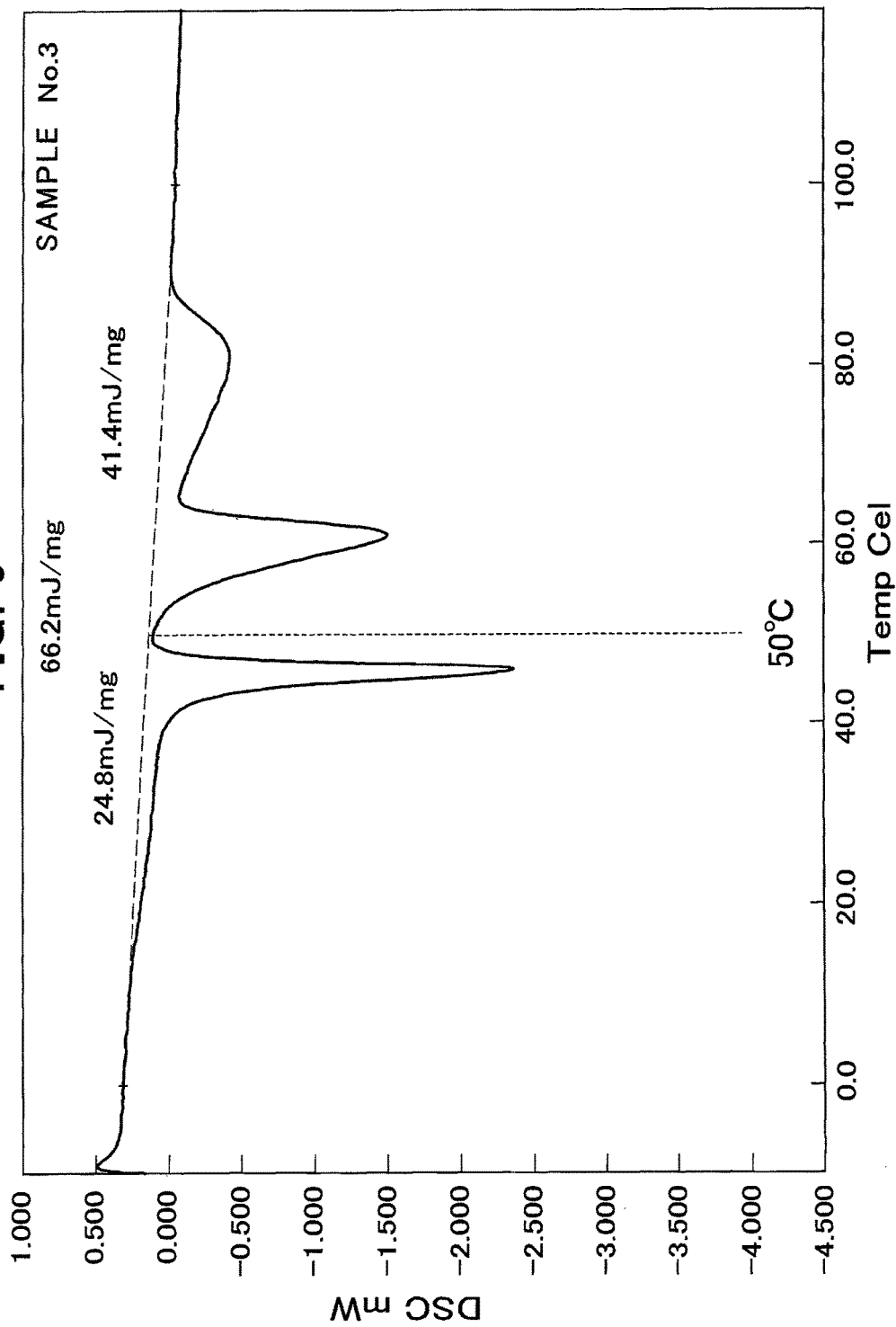
FIG. 9 is a diagram showing the DSC peaks of a mixture of a metastable solid MES and a stable solid MES (sample No. 3, metastable solid/stable solid=43/57).
Figure 10:
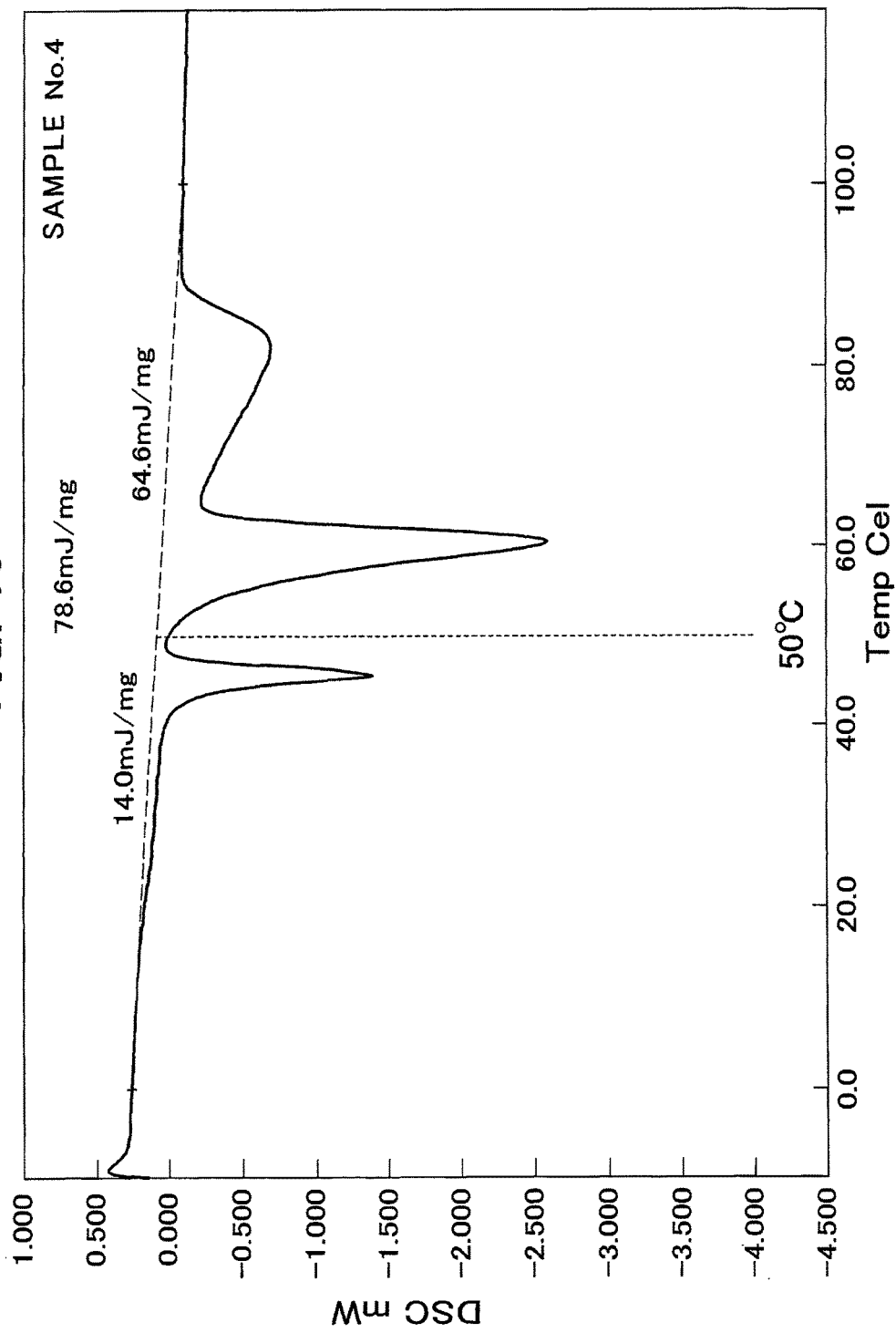
FIG. 10 is a diagram showing the DSC peaks of a mixture of a metastable solid MES and a stable solid MES (sample No. 4, metastable solid/stable solid=13/87).
Figure 11:
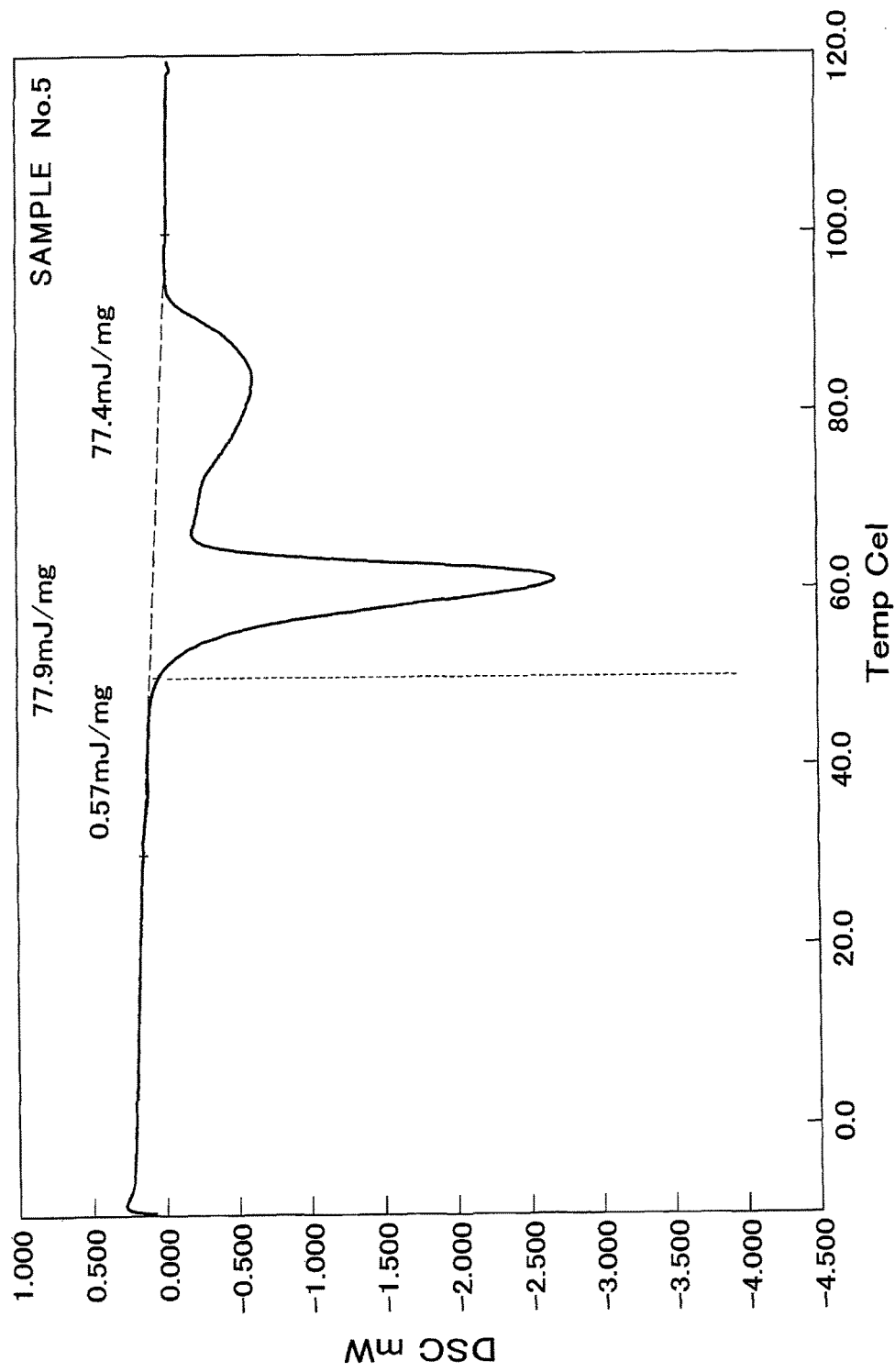
FIG. 11 is a diagram showing the DSC peaks of a stable solid MES (sample No. 5).

The metastable solid MES flakes and stable solid MES flakes previously obtained were subjected to differential scanning thermal analysis. As the differential scanning calorimeter, the instrument "DSC6220" (made by Seiko Instruments Inc.) was used. After 20 g of the MES flakes obtained in Examples and Comparative Examples was crushed using Trio Blender (manufactured by Trioscience K.K.), a sample of 5 to 30 mg was placed in a cell (AG15-CAPSULE). Using alumina as a reference, the sample was heated from 0° C. to 130° C. at a rate of 2° C./min to determine the endotherm and the exotherm. The results are respectively shown in FIG. 7 and FIG. 11.

Based on the thus obtained results, the ratio of the endothermic peak area A at 50 to 130° C. to the whole endothermic peak area B at 0 to 130° C. was obtained.

A/B ratio in the metastable solid MES: 9%

A/B ratio in the stable solid MES: 99%

Examples 1 to 5 and Comparative Examples 1 to 2

The above-mentioned stable solid MES flakes and metastable solid MES flakes were weighed so that the ratio by mass might be 5:95, 25:75, 50:50, 75:25 and 95:5 (respectively in Examples 1 to 5); and 0:100 and 3:97 (respectively in Comparative Examples 1 and 2). Each flake mixture was fed into a pulverizer (Fitzmill, model DKA-3 made by Hosokawa Micron Corporation) and pulverized at 2700 rpm and a throughput of 180 kg/hr, thereby obtaining MES powder mixture. The pulverizing operation was conducted so as to obtain MES powder mixture having a mean particle diameter of about 500 μm, with the inside of the pulverizer being adjusted to 25° C.

Examples 6 to 8 and Comparative Examples 3 to 4

The above-mentioned stable solid MES flakes and metastable solid MES flakes were weighed so that the ratio by mass might be 5:95, 50:50 and 95:5 (respectively in Examples 6 to 8); and 0:100 and 3:97 (respectively in Comparative Examples 3 and 4). Each flake mixture was charged into an agitation granulator (Loedige Mixer M-20, made by Matsubo Corporation) until 50% of the capacity was filled (flake temperature: about 25° C.). The above-mentioned agitation granulator has a horizontal drum therein, and a main shaft, which is disposed parallel to the drum is equipped with a shovel. Independently of the main shaft, there is disposed a chopper in the drum. After the flakes were charged into the granulator, the main shaft was rotated at 200 rpm for 30 seconds, with the chopper being allowed to stand still. Those flakes were thus pulverized and mixed. The pulverizing and mixing operation was conducted so as to obtain MES powder mixture having a mean particle diameter of about 500 μm, with the inside of the granulator being maintained at 25° C.

<Evaluation of Anti-Caking Properties>

Using a yield strength tester (Hang-Up Indicizer, made by Johanson Innovations, Inc.), the yield strength was measured. The yield strength was determined by following the steps shown below.

1. A sample for measurement was heated at 40° C.
2. 30 to 40 g of the sample was weighed and placed into a cell for measurement.
3. Following the display appearing on the screen, "Scientific Mode" was entered as the measuring mode, "15000 Pa" was entered as the compaction pressure, and "25 deg" was entered as the angle of internal friction, to automatically initiate the measurement.
4. After completion of the measurement, the value (Pa) of yield strength displayed on the screen was read. From those values, the anti-caking properties were evaluated on the criteria shown below. The results are shown in Table 1.

<Evaluation Criteria>

∘∘: yield strength of 4000 Pa or less (No caking problem occurs during storage and transportation.)
∘: yield strength of more than 4000 Pa and 5000 Pa or less (Relatively gentle caking problem occurs slightly during storage and transportation.)
Δ: yield strength of more than 5000 Pa and 6000 Pa or less (Relatively gentle caking problem occurs significantly during storage and transportation.)
x: yield strength of more than 6000 Pa (Caking problem occurs during storage and transportation.)

<Determination of Angle of Repose (Fluidity)>

Figure 12:
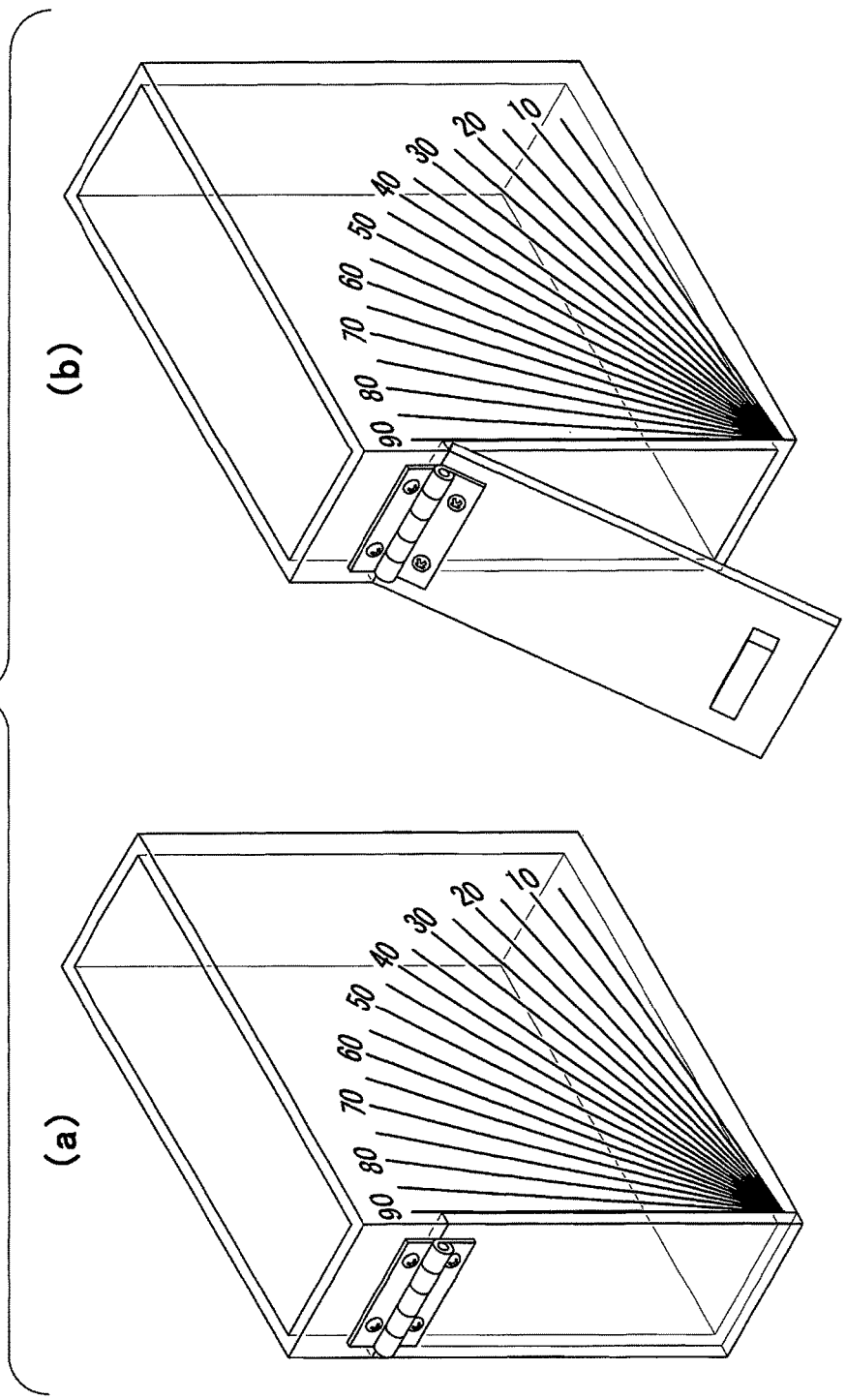
FIG. 12 is a schematic view showing a container for determining the angle of repose.

Immediately after obtaining the powders, 10 kg of the powders were placed into an envelope-shaped paper bag (with a length of 900 mm and a width of 570 mm) lined with a polyethylene inner bag. One minute later, the angle of repose of the powders was determined according to the following method using a measuring apparatus having such a structure as shown in FIG. 12.

As shown in FIG. 12(a), a measuring apparatus 21 is an open-top rectangular parallelepiped constructed by 3-mm-thick transparent acrylic plates, thereby forming an inner space S of 100 mm (W)×200 mm (L)×200 mm (D).

In the measuring apparatus 21, a lower part 22a of the acrylic plate constituting a front wall 22 is designed to pivot in a direction of A about a hinge 24 which is installed on the front wall 22 at a position of 20 mm below the top end thereof so as to open the inner space S of the measuring apparatus 21 forward. On the transparent acrylic plate constituting one of the side walls 26 of the measuring apparatus 21, angle scales 30 turning on the front bottom corner 28 as the central point are printed in a radial manner like a protractor.

(Measuring Method)

From a position of 50 mm above the top of the apparatus, the spray-dried particles P were introduced into the inner space S of the measuring apparatus 21 through the top opening thereof at a flow rate of 0.06 L/sec under the conditions of 25° C. and 40% RH. The inner space S was thus charged with the spray-dried particles P until the particles reached the top end of the inner space S.

After charging, the acrylic apparatus was gently placed on a 100 mm-high platform having a flat upper surface in such a configuration that the open/close front wall side might protrude over the platform. The lower part 22a of the acrylic plate constituting the front wall 22 was allowed to pivot at a rate of 0.5 πrad/s in a direction of A until the angle α reached 90° (as shown in FIG. 12(b)) to gradually open the inner space S forward, thereby letting a part of the spray-dried particles P charged in the inner space S flow therefrom through an opening part 22b. When the flow of the particles stopped, the surface P1 of the spray-dried particles P remaining in the inner space S formed a slope upward from the front bottom corner 28 when viewed from the side wall 26, as shown in FIG. 12(b). The angle of inclination β formed by the surface P1 of the spray-dried particles P remaining in the inner space S of the measuring apparatus 21 was read using the scales 30 indicating the degrees of angle. The procedures mentioned above were repeated three times to take an average. The angle thus obtained was regarded as the angle of repose. The measurement results were rated based on the evaluation criteria shown below. The results are shown in Table 1.

<Evaluation Criteria>

∘∘: less than 60° (good fluidity)
∘: 60° or more and less than 70° (slightly poor fluidity)
Δ: 70° or more and less than 75° (poor fluidity)
x: 75° or more (very poor fluidity)

TABLE 1

<Evaluation Results>

|  |  | Examples | | | | | Comparative Examples | |
| --- | --- | --- | --- | --- | --- | --- | --- | --- |
|  |  | 1 | 2 | 3 | 4 | 5 | 1 | 2 |
| Ratio of stable solid | mass % | 5 | 25 | 50 | 75 | 95 | 0 | 3 |
| Ratio of metastable solid | mass % | 95 | 75 | 50 | 25 | 5 | 100 | 97 |
| Yield strength | [Pa] | 5900 Δ | 5180 Δ | 5580 Δ | 4975 ∘ | 3265 ∘∘ | 10600 x | 8000 x |
| Angle of repose | [°] | 70 Δ | 60 ∘ | 55 ∘∘ | 60 ∘ | 70 Δ | 75 x | 75 x |

|  |  | Examples | | | Comparative Examples | |
| --- | --- | --- | --- | --- | --- | --- |
|  |  | 6 | 7 | 8 | 3 | 4 |
| Ratio of stable solid | mass % | 5 | 50 | 95 | 0 | 3 |
| Ratio of metastable solid | mass % | 95 | 50 | 5 | 100 | 97 |
| Yield strength | [Pa] | 5690 Δ | 5240 Δ | 3800 ∘∘ | 11050 x | 7590 x |
| Angle of repose | [°] | 70 Δ | 60 ∘ | 65 ∘ | 75 x | 75 x |

TEST EXAMPLES

The α-SF salt metastable solid flakes and the α-SF salt stable solid powder obtained in Preparation Example 1 were mixed at mixing ratios as shown in Table 2. The resultant mixtures were subjected to differential scanning thermal analysis in the same manner as previously explained. The results are shown in Table 2 and FIGS. 7 to 11.

TABLE 2

| Sample No. | Mass (mg) used for mixture Metastable solid | Mass (mg) used for mixture Stable | Metastable solid/Stable solid (mass ratio) | DSC Calorie (mJ/mg) <50° C. | DSC Calorie (mJ/mg) ≥50° C. | Ratio of Calorie (%) ≥50° C./ whole |
|---|---|---|---|---|---|---|
| 1 | 12.0 | 0 | 100/0 | 53.8 | 5.3 | 9.0 |
| 2 | 7.4 | 5.1 | 59/41 | 35.3 | 32.7 | 48.1 |
| 3 | 5.5 | 7.2 | 43/57 | 24.8 | 41.4 | 62.5 |
| 4 | 1.7 | 11.1 | 13/87 | 14.0 | 64.6 | 82.2 |
| 5 | 0 | 12.2 | 0/100 | 0.57 | 77.4 | 99.3 |

Examples 9 to 14

The α-SF-Na metastable solid flakes and stable solid flakes obtained in Preparation Example 1, and zeolite were continuously fed into the hopper of a continuous kneader (KRC-kneader, Model S-2, made by Kurimoto, Ltd.) at mixing ratios as shown in Table 3. The temperature of each material was 25° C. when the material was fed. The feed rate was within the range of 50 to 120 kg/h in total (of stable solid flakes, metastable solid flakes and zeolite). Water of 80° C. (at the inlet) was allowed to flow through the jacket. The kneading operation was carried out with the main shaft of the kneader being rotated at 100 rpm. (The shear rate was 600 (l/s).)

After completion of the kneading operation, the kneaded product was discharged from the outlet of the kneader. The temperature of the kneaded product thus obtained was 65° C. The kneaded product was continuously fed into a granulator "Pelleter Double EXDF-100" (made by Dalton Corporation) at a feed rate of 50 to 120 kg/h to be extruded through a die with a diameter of 0.8 or 5 mm. The noodle-like MES thus extruded was continuously carried onto a band type cooler (made by Maezawa Industries, Inc., with a width of 200 mm and a length of 4 m, equipped with three circulating fans) where the band speed might be controlled to be the same as the extrusion speed. The noodle-like MES was thus cooled. In this case, the space velocity of cooling air above the upper (lower) surface of the band was controlled to 1.2 m/s by adjusting the volume of air (circulating fans), and then the temperature of cooling air at the inlet of the band type cooler was adjusted to 18 to 20° C. by controlling the ratio of newly charged cooling air to the cooling air circulating in the cooler. The average temperature of the exhaust at the outlet of the band type cooler was controlled to 26 to 28° C. by adjusting the feed rate of each raw material and setting the band velocity of the band type cooler to the feed rate.

Criteria for Judging:
(Cooling Capacity)

The feed rate of each material and the band velocity of the band type cooler were adjusted in order to decrease the temperature of the fatty acid alkyl ester sulfonate metal salt-containing product to 26 to 28° C. at the outlet of the band type cooler. The thus obtained feed rate (i.e., production capacity) was evaluated as the cooling capacity of the band type cooler. The results are shown in Table 3.

(Evaluation Criteria)
∘∘: Production capacity of 100 kg/h or more (very high cooling capacity)
∘: Production capacity of 80 kg/h or more and less than 100 kg/h (high cooling capacity)
Δ: Production capacity of 50 kg/h or more and less than 80 kg/h (medium cooling capacity)
x: Production capacity of less than 50 kg/h (low cooling capacity)

<Solubility Test>

The fatty acid alkyl ester sulfonate metal salt-containing product was ground in a speed mill and sieved to obtain particles with a particle diameter of 1 mm or less. Using those particles, a test for determining the solubility from residue was conducted as shown below.

One liter of tap water was put into a 1-L beaker, and a three-one motor was prepared which was equipped with a stirring rod where one agitating blade with a height of 40 mm and a width of 20 mm was attached to the end of the shaft. The tap water in the beaker was adjusted to 20° C. in a water bath of 20° C. The motor was set in the beaker so that the agitating blade might be disposed 1 cm above from the bottom of the beaker. While rotating the agitating blade at 250 rpm, the fatty acid alkyl ester sulfonate metal salt-containing particles (5 g) were gradually added into the water. After completion of the addition, agitation was continued for 10 minutes. The sample solution thus obtained was filtered through a nylon tricot cloth which was weighed in advance. The insoluble residue was filtered out, and the nylon tricot cloth to which the insoluble residue was attached was dried in a dryer. The weight of the dried cloth was determined. From the weight of the dried nylon tricot cloth the initial weight determined in advance was subtracted, thereby obtaining the dry weight of the insoluble residue. By substituting the above-mentioned dry weight into the following equation: [insoluble residue (%)=dry weight/5 g×100], the insoluble residue (%) was calculated. The results are shown in Table 3.

(Evaluation Criteria)
∘∘: Insoluble residue of less than 10%
∘: Insoluble residue of 10% or more and less than 20%
Δ: Insoluble residue of 20% or more and less than 30%
x: Insoluble residue of 30% or more

TABLE 3

| | | Examples 9 | Examples 10 | Examples 11 | Examples 12 | Examples 13 | Examples 14 |
|---|---|---|---|---|---|---|---|
| Ratio of stable solid | [mass %] | 7 | 11 | 41 | 81 | 3 | 19 |
| Ratio of metastable solid | [mass %] | 90 | 80 | 50 | 10 | 80 | 80 |
| Zeolite | mass % | 3 | 9 | 9 | 9 | 17 | 1 |
| Yield strength | [Pa] | 5700 | 5280 | 4700 | 4030 | 5890 | 5110 |
| | | Δ | Δ | ∘ | ∘ | Δ | Δ |
| Angle of repose | [°] | 65 | 60 | 65 | 65 | 70 | 65 |
| | | ∘ | ∘ | ∘ | ∘ | Δ | ∘ |
| Cooling capacity | [kg/hr] | 123 | 118 | 123 | 134 | 91 | 120 |
| | | ∘∘ | ∘∘ | ∘∘ | ∘∘ | ∘ | ∘∘ |
| Solubility test | [wt %] | 5.2 | 5.6 | 5.2 | 4.9 | 4.2 | 22.3 |
| | | ∘∘ | ∘∘ | ∘∘ | ∘∘ | ∘∘ | Δ |

The metastable solid α-SF salt and the stable solid α-SF salt used in the mixtures of Examples 10 to 12 were mixed at the mixing ratios as shown in Table 4. The resultant mixtures were subjected to the differential scanning thermal analysis in the same manner as previously explained. The results are shown in Table 4.

TABLE 4

| Examples | Ratio of metastable solid to stable solid prior to mixing (ratio by mass) | DSC Calorie (mJ/mg) <50° C. | DSC Calorie (mJ/mg) ≧50° C. | Ratio of Calorie (%) ≧50° C./whole |
|---|---|---|---|---|
| 10 | 88/12 | 27.6 | 40.3 | 59.4 |
| 11 | 55/45 | 19.8 | 51.1 | 72.1 |
| 12 | 11/89 | 13.8 | 52.8 | 79.3 |

REFERENCE SIGNS LIST

11 Mixing container
12 Driving apparatus
13 Agitating shaft
14, 15 Agitating blade
16 Baffle plate
17 Jacket
21 Measuring apparatus
30 Angle scales
P Spray-dried particles
β Angle of inclination

The invention claimed is:

1. A solid mixture of a solid fatty acid alkyl ester sulfonate metal salt mixture consisting of:
 (a) a solid fatty acid alkyl ester sulfonate metal salt, which is a metastable solid, having an endothermic peak area at 50 to 130° C. of less than 50% relative to the whole endothermic peak area at 0 to 130° C. as measured on a differential scanning calorimeter, and
 (b) a solid fatty acid alkyl ester sulfonate metal salt, which is a stable solid, having an endothermic peak area at 50 to 130° C. of 50% or more relative to the whole endothermic peak area at 0 to 130° C. as measured on a differential scanning calorimeter,
 with a ratio of (a) to (b) by mass of 95/5 to 5/95,
 wherein the fatty acid alkyl ester sulfonate metal salt is a mixture of the fatty acid alkyl ester sulfonate metal salt represented by formula (1) wherein $R^1$ is a straight-chain or branched alkyl or alkenyl group having 14 carbon atoms and the fatty acid alkyl ester sulfonate metal salt represented by formula (1) wherein $R^1$ is a straight-chain or branched alkyl or alkenyl group having 16 carbon atoms:

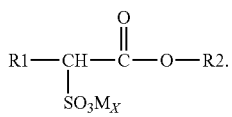

(1)

2. A solid mixture of a solid fatty acid alkyl ester sulfonate metal salt mixture consisting of:
 (a) a solid fatty acid alkyl ester sulfonate metal salt, which is a metastable solid, having an endothermic peak area at 50 to 130° C. of less than 50% relative to the whole endothermic peak area at 0 to 130° C. as measured on a differential scanning calorimeter, and
 (b) a solid fatty acid alkyl ester sulfonate metal salt, which is a stable solid, having an endothermic peak area at 50 to 130° C. of 50% or more relative to the whole endothermic peak area at 0 to 130° C. as measured on a differential scanning calorimeter,
 with a ratio of (a) to (b) by mass of 80/20 to 5/95,
 wherein the fatty acid alkyl ester sulfonate metal salt is a mixture of the fatty acid alkyl ester sulfonate metal salt represented by formula (1) wherein $R^1$ is a straight-chain or branched alkyl or alkenyl group having 14 carbon atoms and the fatty acid alkyl ester sulfonate metal salt represented by formula (1) wherein $R^1$ is a straight-chain or branched alkyl or alkenyl group having 16 carbon atoms:

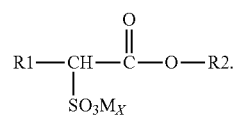

(1)

3. The solid mixture of claim 1, wherein the fatty acid alkyl ester sulfonate metal salt (b) has the endothermic peak area at 50 to 130° C. of 70% or more relative to the whole endothermic peak area at 0 to 130° C. as measured on a differential scanning calorimeter.

4. The solid mixture of claim 1, wherein the mixture is in a powder form.

5. A detergent composition comprising the solid mixture of claim 1.

6. A method for producing a fatty acid alkyl ester sulfonate metal salt powder mixture, comprising the steps of:
 mixing (a) a fatty acid alkyl ester sulfonate metal salt, which is a metastable solid, having an endothermic peak area at 50 to 130° C. of less than 50% relative to the whole endothermic peak area at 0 to 130° C. as measured on a differential scanning calorimeter, and
 (b) a fatty acid alkyl ester sulfonate metal salt, which is a stable solid, having an endothermic peak area at 50 to 130° C. of 50% or more relative to the whole endothermic peak area at 0 to 130° C. as measured on a differential scanning calorimeter,
 wherein the fatty acid alkyl ester sulfonate metal salt is a mixture of the fatty acid alkyl ester sulfonate metal salt represented by formula (1) wherein $R^1$ is a straight-chain or branched alkyl or alkenyl group having 14 carbon atoms and the fatty acid alkyl ester sulfonate metal salt represented by formula (1) wherein $R^1$ is a straight-chain or branched alkyl or alkenyl group having 16 carbon atoms:

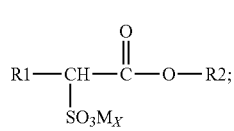

(1)

and
 pulverizing the mixture to obtain the fatty acid alkyl ester sulfonate metal salt powder mixture with a ratio of (a) to (b) by mass of 95/5 to 5/95, wherein the mixing step and the pulverizing step may be carried out in the reverse order.

* * * * *